US007592317B1

(12) United States Patent
Weichselbaum et al.

(10) Patent No.: US 7,592,317 B1
(45) Date of Patent: Sep. 22, 2009

(54) CONSTITUTIVE GENE EXPRESSION IN CONJUCTION WITH IONIZING RADIATION

(75) Inventors: Ralph H. Weichselbaum, Chicago, IL (US); Dennis E. Hallahan, Park Ridge, IL (US); Donald W. Kufe, Wellesley, MA (US); Vikas P. Sukhatme, Newton Centre, MA (US)

(73) Assignees: The University of Chicago, Chicago, IL (US); Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 08/289,290

(22) Filed: Aug. 11, 1994

(51) Int. Cl.
 *A61K 31/70* (2006.01)
 *C12N 15/09* (2006.01)
(52) U.S. Cl. ........................ 514/44; 435/455
(58) Field of Classification Search ............... 514/44; 435/172.3, 320.1, 240.2; 424/93.21; 530/351
 See application file for complete search history.

(56) References Cited

U.S. PATENT DOCUMENTS

| 4,677,063 | A | | 6/1987 | Mark et al. ............... 435/68 |
| 5,264,618 | A | * | 11/1993 | Felgner et al. ............ 560/224 |
| 5,935,935 | A | * | 8/1999 | Connelly et al. ........... 514/44 |
| 6,143,290 | A | * | 11/2000 | Zhang et al. |
| 6,228,356 | B1 | * | 5/2001 | Glorioso et al. ........... 424/93.2 |

FOREIGN PATENT DOCUMENTS

| WO | WO9211033 | * | 7/1992 |
| WO | WO 94/06916 | | 3/1994 |

OTHER PUBLICATIONS

Brown. D. The Washington Post (Dec. 8, 1995) pp. A1.A22.*
Blaese, M. et al. Cancer Gene Therapy 2(4): 291-297 (1995).*
Marshall, E. Science 269 : 1050-1055 (1995).*
Miller et al (1995) FASEB J 9: 190-199.*
Culver et al (1994) Trends in Genetics 10: 174-178.*
Hodgson (1995) Exp Opin Ther Patents 5: 459-468.*
Arai et al (1990) Ann Rev Biochem 59: 783-785.*
Vile et al (1993) Cancer Research 53: 962-967.*
Breakefield et al (1991) New Biologist 3: 203-218.*
Mattern et al (1988) Cancer and Metastasis Reviews 7: 263-284.*
Uzvolgyi et al. Reintroduction of a normal retinoblastoma gene into retinoblastoma and ostrosarcoma cells inhibits the replication associated function of SV40 large T antigen vol. 2, pp. 297-303 Jun. 1991.*
Walther et al. Retrovirus-mediated gene transfer of tumor necrosis factor alpha into colon carcinoma cells generates a growth inhibition pp. 1565-1574 1993.*
Baumann et al., "Response of Xenografts of Human Malignant Gliomas and Squamous Cell Carcinomas to Fractionated Irradiation," *J. Radiation Oncology Biol. Phys.*, 23:803-809, 1992.
Beutler and Cerami, "Tumor Necrosis, Cachexia, Shock, and Inflammation: A Common Mediator," *Ann. Rev. Biochem.*, 57:505-518, 1988.

Brach et al., "Ionizing Radiation Induces Expression and Binding Activity of the Nuclear Factor KB," *J. Clin. Invest.*, 88:691-695, 1991.
Budach et al., "The $TCD_{50}$ and Regrowth Delay Assay in Human Tumor Xenografts: Differences and Implications," *Int. J. Radiation Oncology Biol. Phys.*, 25, 259-268, 1993.
Chou and Roizman, "The $\gamma_1 34.5$ Gene of Herpes Simplex Virus 1 Precludes Neuroblastoma Cells from Triggering Total Shutoff of Protein Synthesis Characteristic of Programmed Cell Death in Neuronal Cells," *Proc. Natl. Acad. Sci. USA*, 89:3266-3270, 1992.
Datta et al., "Involvement of Reactive Oxygen Intermediates in the Induction of c-jun Gene Transcription by Ionizing Radiation," *Biochemistry*, 31:8300-8306, 1992.
Datta et al., "Reactive Oxygen Intermediates Target $CC(A/T)_6GG$ Sequences to Mediate Activation of the Early Growth Response 1 Transcription Factor Gene by Ionizing Radiation," *Proc. Natl. Acad. Sci. USA*, 90:2419-2422, 1993.
Datta et al., "Ionizing Radiation Activates Transcription of the *EGR1* gene via CArG Elements," *Proc. Natl. Acad. Sci. USA*, 89:10149-10153, 1992.
Gashler et al., "A Novel Repression Module, and Extensive Activation Domain, and a Bipartite Nuclear Localization Signal Defined in the Immediate-Early Transcription Factor Egr-1," *Molecular and Cellular Biology*, 13 (8) :4556-4571, 1993.
Ghosh-Choudhury, "Protein IX, a Minor Component of the Human Adenovirus Capsid, is Essential for the Packaging of Full Length Genomes," *EMBO Journal*, 6(6) :1733-1739. 1987.
Gomez-Foix et al., "Adenovirus-mediated Transfer of the Muscle Glycogen Phosphorylase Gene into Hepatocytes Confers Altered Regulation of Glycogen Metabolism," *J. Biol. Chem.*, 267 (35) :25129-25134, 1992.
Graham and Prevec, "Adenovirus-based Expression Vectors and Recombinant Vaccines," *Biotechnology*, 20:363-390, 1992.
Hallahan et al., "Increased Tumor Necrosis Factor $\alpha$ mRNA After Cellular Exposure to Ionizing Radiation," *Proc. Natl. Acad. Sci. USA*, 86:10104-10107, 1989.
Hallahan et al., "Transcriptional regulation of the TNF gene by x-irradiation," *Proc. Am. Assoc. Cancer Res.*, 31:75, 1990.
Hallahan et al., "The Interaction Between Recombinant Human Tumor Necrosis Factor and Radiation in 13 Human Tumor Cell Lines," *Int. J. Radiation Oncology Biol. Phys.*, 19:69-74, 1990.
Hallahan et al., "Phase I Dose Escalation Study of Tumor Necrosis Factor and Radiation," *International Journal of Radiation Oncology Biology, Physics*, 27(1) :184 Abstract 94, 1993.

(Continued)

*Primary Examiner*—Q. Janice Li
(74) *Attorney, Agent, or Firm*—Michael Best & Friedrich LLP

(57) ABSTRACT

The present disclosure demonstrates the successful use of constitutive promoters operatively linked to genes encoding radiosensitizing or radioprotecting factors, administered to cells, tissues, or patients in conjunction with radiation exposure. Also disclosed are pharmacological preparations to be used to increase the levels of radiosensitizing compounds such as TNF-$\alpha$, or radioprotective compounds such as MnSOD, in specified tissues or tumors of a subject.

30 Claims, No Drawings

OTHER PUBLICATIONS

Hallahan et al., "Radiation Signaling Mediated by Jun Activation Following Dissociation from a Cell Type-Specific Repressor," *J. Biol. Chem.*, 268 (7) :4903-4907, 1993.

Herz and Gerard, "Adenovirus-mediated Transfer of Low Density Lipoprotein Receptor Gene Acutely Accelerates Cholesterol Clearance in Normal Mice," *Proc. Natl. Acad. Sci. USA*, 90 :2812-2816, 1993.

Le Gal Lasalle et al., "An Adenovirus Vector for Gene Transfer into Neurons and Glia in the Brain," *Science*, 259:988-990, 1993.

Levero et al., Defective and Nondefective Adenovirus Vectors for Expressing Foreign Genes In Vitro and In Vivo, *Gene*, 101:195-202, 1991.

Neta and Oppenheim, "Radioprotection with Cytokines-Learning from Nature to cope with Radiation Damage," *Cancer Cells*, 3(10) :391-396, 1991.

Nicolau et al., "In Vivo Expression of Rat Insulin After Intravenous Administration of the Liposome-entrapped Gene for Rat Insulin I," *Proc. Natl. Acad Sci. USA*, 80:1068-1072, 1983.

Post and Roizman, "A Generalized Technique for Deletion of Specific Genes in Large Genomes: α Gene 22 of Herpes Simplex Virus 1 is Not Essential for Growth," *Cell*, 25:227-232, 1981.

Ragot et al., "Efficient Adenovirus-Mediated Transfer of a Human Minidystrophin Gene to Skeletal Muscle of *mdx* Mice," *Nature*, 361:647-650, 1993.

Reid et al., "Resistance to Killing by Tumor Necrosis Factor in an Adipocyte Cell Line Caused by a Defect in Arachidonic Acid Biosynthesis," *J. Biol. Chem.*, 266(25) :16580-16597, 1991.

Rich et al., "Development and Analysis of Recombinant Adenoviruses for Gene Therapy of Cystic Fibrosis," *Gene Ther.*, 4:461-476, 1993.

Roizman and Sears, "Herpes Simplex Viruses and Their Replication," *Virology*, 2nd Edition, Chapter 65: 1795-1841, 1990.

Sherman et al., "Ionizing radiation regulates expression of the c-jun proto-oncogene," *Proc. Am. Assoc. Cancer Res.*, 31:13, 1990.

Tartaglia and Goeddel, "Two TNF Receptors," *Immunology Today*, 13(5) :151-153, 1992.

Tartaglia et al., "Tumor Necrosis Factor's Cytotoxic Activity is Signaled by the p55 TNF Receptor," *Cell*, 73:213-216, 1993.

Tartaglia et al., "A Novel Domain Within the 55 kd TNF Receptor Signals Cell Death," *Cell*, 74:845-853, 1993.

Tartaglia and Goeddel, "Tumor Necrosis Factor Receptor Signaling," *J. Biol. Chem.*, 267(7) :4304-4307, 1992.

Teng et al., "Long-term Inhibition of Tumor Growth by Tumor Necrosis Factor in the Absence of Cachexia or T-cell Immunity," *Proc. Natl. Acad. Sci. USA*, 88:3535-3539, 1991.

Weichselbaum, "Possible Applications of Biotechnology to Radiotherapy," *Eur. J. Cancer*, 27(4) :405-407, 1991.

Weichselbaum et al., "Biological Consequences of Gene Regulation After Ionizing Radiation Exposure," *J. of the National Cancer Institute*, 83 (7) :480-484, 1991.

Weichselbaum et al., "Gene Therapy Targeted by Ionizing Radiation," *Int. J. Radiation Oncology Biol. Phys.*, 24:565-567, 1992.

Weichselbaum et al., "Inherently Radioresistant Cells Exist in Some Human Tumors," *Proc. Natl. Acad. Sci. USA*, 82:4732-4735, 1985.

Wong et al., "Antiviral Activity of Tumor Necrosis Factor (TNF) is Signaled Through the 55-dKa Receptor, Type I TNF," *J. of Immunology*, 149 (10) :3350-3353, 1992.

Abou-Shoer et al., Flavonoids From *Koelreuteria henryi* And Other Sources As Protein-Tyrosine Kinase Inhibitors, *J. Nat. Proc.*, 56(6):967-9, 1993.

Alexandropoulos et al., "v-Fps-Responsiveness in the Egr-1 Promoter is Mediated by Serum Response Elements," *Nucleic Acids Research*, 20(9):2355-2359, 1992.

Al-Khodiary and Carr, DNA repair mutants defining $G_2$ checkpoint pathways in *Schizosaccharomyces pombe*, *The EMBO Journal*, 11(4):1343-1350, 1992.

Angel et al., "The *jun* Proto-Oncogene is Positively Autoregulated by its Product, Jun./AP-1," *Cell*, 55:875-885, 1988.

Atherton-Fessler et al., "Mechanisms of $p34^{cdc2}$ Regulation," *Molecular and Cellular Biology*, 13(3):1675-1685, 1993.

Attar et al., "Expression Cloning of a Novel Zinc Finger Protein that Binds to the c-fos Serum Response Element," *Molecular and Cellular Biology*, 12(5):2432-2443, 1992.

Barbet and Carr, "Fission yeast *wee1*protein kinase is not required for DNA damage-dependent mitotic arrest," *Nature*, 364:824-827, 1993.

Bhuyan et al., "Lethality, DNA Alkylation, and Cell Cycle Effects of Adozelesin (U-73975) on Rodent and Human Cells," *Cancer Research*, 52:5687-5692, 1992.

Boothman et al., "Identification and Characterization of X-Ray-Induced Proteins in Human Cells," *Cancer Research*, 49:2871-2878, 1989.

Buchdunger et al., "4,5-Dianilinophthalimide: A protein-tyrosine kinase inhibitor with selectivity for the epidermal growth factor receptor signal transduction pathway and potent in vivo antitumor activity," *Proc. natl. Acad. Sci. USA*, 91:2334-2338, 1994.

Cantley et al., Oncogenes and Signal Transduction, *Cell*, 64:281-302, 1991.

Chan et al., "Selective inhibition of the growth of ras-transformed human bronchial epithelial cells by emodin, a protein-tyrosine kinase inhibitor," *Biochemical and Biophysical Research Communications*, 193(3):1152-1158, 1993.

Chen et al., "Structure of malhamensilipin A, an inhibitor of protein tyrosine kinase, from the cultured chrysophyte *Poterioochromonas malhamensis*," *Journal of Natural Products*, 57(4):524-527, 1994.

Devary et al., "The Mammalian Ultraviolet Response is Triggered by Activation of Src Tyrosine Kinases," *Cell*, 71:1081-1091, 1992.

Enoch and Nurse, "Mutation of Fission Yeast Cell Cycle Control Genes Abolishes Dependence of Mitosis on DNA Replication," *Cell*, 60:665-673, 1990.

Gillespie et al., "Inhibition of pancreatic cancer cell growth in vitro by the tyrphostin group of tyrosine kinase inhibitors," *Br. J. Cancer*, 68:1122-1126, 1993.

Gould et al., "Complementation of the Mitotic Activator, $p80^{cdc25}$, by a Human Protein-Tyrosine Phosphatase," *Science*, 250:1573-1576, 1990.

Gubits et al., "Expression of Immediate Early Genes after Treatment of Human Astrocytoma Cells with Radiation and Taxol," *Int. J. Radiation Oncology Biol. Phys.*, 27(3):637-642, Oct. 1993.

Gustafson et al., "Hydrogen Peroxide Stimulates Phospholipase $A_2$-Mediated Archidonic Acid Release in Cultured Intestinal Epithelial Cells (INT 407)," *Archidonic Acid Release*, 26:237-247, 1991.

Hallahan et al., "Inhibition of Protein Kinases Sensitizes Human Tumor Cells to Ionizing Radiation," *Radiation Research*, 129:345-350, 1992.

Hallahan et al., "Ketoconazole Attenuates Radiation-Induction of Tumor Necrosis Factor," *Int. J. Radiation Oncology*, in press, 1994.

Hallahan et al., "Mechanisms of X-Ray Mediated Protooncogene c-*jun* Expression in Radiation-Induced Human Sarcoma Cell Lines," *Int. J. Radiation Oncology Biol. Phys.*, 21(6):1677-1681, 1991.

Hallahan et al., "Membrane-Derived Second Messenger Regulates X-Ray-Mediated Tumor Necrosis Factor a Gene Induction," *Proc. Natl. Acad. Sci. USA*, 91:4897-4901, May 1994.

Hallahan et al., "Protein kinase C mediates x-ray inducibility of nuclear signal transducers EGR1 and JUN," *Proc. Natl. Acad. Sci. USA*, 88:2156-2160, 1991.

Hallahan et al., "The Role of Cytokines in Radiation Oncology," *Important Advances in Oncology*, 1993.

Hallahan et al., "Tumor Necrosis Factor Gene Expression Is Mediated by Protein Kinase C following Activation by Ionizing Radiation," *Cancer Research*, 51:4565-4569, 1991.

Hartley et al., "DNA sequence selectivity of guanine-N7 alkylation by nitrogen mustards is preserved in intact cells," *Nucleic Acids Research*, 20(12):3175-3178, 1992.

Hartwell and Weinert, "Checkpoints: Controls that Ensure the Order of Cell Cycle Events," *Science*, 246:629-634, 1989.

Hempel et al., "Tyrosine Phosphorylation of Phospholipase $C-1_2$ upon Cross-linking of Membrane Ig on Murine B Lymphocytes," *The Journal of Immunology*, 148(10):3021-3027, 1992.

Herrlich et al., "DNA Damage-Induced Gene Expression: Signal transduction and Relation to Growth Factor Signaling," *Rev. Physiol. Biochem. Pharmacol.*, 119:187-223, 1992.

Hollander and Fornace, "Induction of fos RNA by DNA-damaging Agents," *Cancer Research*, 49:1687-1692, 1989.

Hsu et al., "Inhibition Kinetics and Selectivity of the Tyrosine Kinase Inhibitor Erbstatin and a Pyridone-Based Analogue," *Biochemical Pharmacology*, 43(11):2471-2477, 1992.

Hwu et ak., "Functional and Molecular Characterization of Tumor-Infiltrating Lymphocytes Transduced with Tumor Necrosis Factor-a cDNA for the Gene Therapy of Cancer in Humans," *The Journal of Immunology*, 150(9):4104-4115, May 1993.

Jayasuriya et al., "Emodin, A Protein Tyrosine Kinase Inhibitor From *Polygonum cuspidatum*," *J. Nat. Proc.*, 55(5):696-8, 1992.

Kastan et al., "Participation of p53 Protein in the Cellular Response to DNA Damage," *Cancer Research*, 51:6304-6311, 1991.

Lambert and Borek, "X-ray-Induced Changes in Gene Expression in Normal and Oncogene-Transformed Rat Cell Lines," *Journal of the National Cancer Institute*, 80(18):1492-1497, 1988.

Luna et al., "Photodynamic Therapy Mediated Induction of Early Response Genes," *Cancer Research*, 54(5):1374-1380, Mar. 1994.

Mustelin and Altman, "Dephosphorylation and Activation of the T Cell Tyrosine Kinase $pp56^{lck}$ by the leukocyte common antigen (CD45)," *Oncogene*, 5:809-813, 1990.

Neta et al., "Role of Interleukin 6 (IL-6) in Protection from Lethal Irradiation and in Endocrine Responses to IL-1 and Tumor Necrosis Factor," *The Journal of Experimental Medicine*, 175:689-694, 1992.

Nurse, "Universal Control Mechanism Regulating Onset of M-Phase," *Nature*, 344:503-508, 1990.

Okabe et al., "BE-23372M, A Novel Protein Tyrosine Kinase Inhibitor I. Producing Organism, Fermentation, Isolation and Biological Activities," *The Journal of Antibiotics*, 47(3):289-293, 1994.

Papathanasiou et al., "Identification of an x-ray-inducible human gene and its altered expression in ataxia telangiectasia," *Proceedings of the American Association for Cancer Research*, 31:304, 1990.

Pleiman et al., "Mapping of Sites on the Src Family Protein Tyrosine Kinases $p55^{blk}$, $p59^{fyn}$, and $p56^{lyn}$ Which Interact with the Effector Molecules Phospholipase C-g, Microtubule-Associated Protein Kinase, GTPase-Activating Protein, and Phosphatidylinositol 3-Kinase," *Molecular and Cellular Biology*, 13(9):5877-5887, 1993.

Rewcastle et al., "Tyrosine Kinase Inhibitors. 3. Structure-Activity Relationships for Inhibition of Protein Tyrosine Kinases by Nuclear-Substituted Derivatives of 2,2'-Dithiobis (1-methyl-*N*-phenyl-1*H*-indole-3-carboxamide)," *J. Med. Chem.*, 37:2033-2042, 1994.

Sherman et al., "Regulation of Tumor Necrosis Factor Gene Expression by Ionizing Radiation in Human Myeloid Leukemia Cells and Peripheral Blood Monocytes," *The American Society for Clinical Investigation, Inc.*, 87:1794-1797, 1991.

Sukhatme et al., "A Zinc Finger-Encoding Gene Coregulated with c-fos During Growth and Differentiation, and After Cellular Depolarization," *Cell*, 53:37-43, 1988.

Uckun et al., "Ionizing Radiation Stimulates Unidentified Tyrosine-Specific Protein Kinases in Human B-Lymphocyte Precursors, Triggering Apoptosis and Clonogenic Cell Death," *Proc. Natl. Acad. Sci. USA*, 89:9005-9009, Oct. 1992.

Uckun et al., "Tyrosine phosphorylation is a mandatory proximal step in radiation-induced activation of the protein kinase C signaling pathway in human B-lymphocyte precursors," *Proc. Natl. Acad. Sci. USA*, 90:252-256, 1993.

Ward et al., "The Effect of Steroids on Radiation-Induced Lung Disease in the Rat," *Rad. Res.*, 136:22-28, 1993.

Ward et al., "The Pulmonary Response to Sublethal Thoracic Irradiation in the Rat," *Rad. Res.*, 136:15-21, 1993.

Weichselbaum et al., "Gene Therapy Targeted by Radiation Preferentially Radiosensitizes Tumor Cells," *Cancer Research*, 54:4266-4269, Aug. 1994.

Weichselbaum et al., "In Vitro Radiobiological Parameters of Human Sarcoma Cell Lines," *Int. J. Radiation Oncology Biol. Phys.*, 15:937-942, 1988.

Weichselbaum et al., "Radiation induction of immediate early genes: effectors of the radiation-stress response." *Int. J. Rad. Oncol.*, 30:229-234, 1994.

Weichselbaum et al., "Radiation-resistant and repair-proficient human tumor cells may be associated with radiotherapy failure in head- and neck-cancer patients," *Proc. Natl. Acad. Sci. USA*, 83:2684-2688, 1986.

Weichselbaum et al., "X-Ray Sensitivity of Fifty-three Human Diploid Fibroblast Cell Strains from Patients with Characterized Genetic Disorders," *Cancer Research*, 40:920-925, 1980.

Witte et al., Effects of Irradiation on the Release of Growth Factors from Cultured Bovine, Porcine, and Human Endothelial Cells, *Cancer Research*, 49:5066-5072, 1989.

Yamanashi et al., "Activation of Src-like protein-tyrosine kinase Lyn and its association with phosphatidylinositol 3-kinase upon C-cell antigen receptor-mediated signaling," *Proc. Natl. Acad. Sci. USA*, 89:1118-1122, 1992.

Zhou and Elledge, "Isolation of crt Mutants Constitutive for Transcription of the DNA Damage Inducible Gene *RNR3* in *Saccharomyces cerevisiae*," *Genetics* 131:851-866, 1992.

International Search Report dated Dec. 8, 1995.

* cited by examiner

CONSTITUTIVE GENE EXPRESSION IN CONJUCTION WITH IONIZING RADIATION

The government may own rights in the present invention pursuant to NIH grant numbers CA58508, CA41068, CA40046, and CA42586.

BACKGROUND OF THE INVENTION

1. Field of the Invention

The field of this invention generally encompasses radiation induced cell damage and, more particularly, a process of sensitizing tumor cells to the effects of ionizing radiation or protecting nontumor cells from radiation exposure.

2. Description of the Related Art

Radiation of tumor or cancerous cells is a well established and standard therapeutic regimen. Although all of the mechanisms by which radiation affects these cells have not yet been elucidated, certain aspects of radiation induced tumor cell toxicity have been described.

Tumor necrosis factor (TNF), originally identified because of its anti-tumor activity (Carswell et al., 1975), is a pleiotropic biological effector that regulates the activation of genes (Old, 1988; Beutler et al., 1988). Cellular responses mediated by TNF-α include anti-viral and immunoregulatory activity, as well as neutrophil adhesion to vascular endothelial cells. Clinical manifestations of aberrant TNF-α production include cachexia, respiratory distress syndrome and septic shock (Beutler et al., 1988). While TNF-α interacts with two specific cell surface receptors (Tartaglia et al., 1992), many TNF dependent events, including cytotoxicity, are mediated by the 55 Kd receptor, TNF $R_1$ (Wong et al., 1992; Tartaglia et al., 1992; Tartaglia et al., 1993; Tartaglia et al., 1993). The killing action of TNF-α is proposed to occur following receptor binding and production of superoxide and hydroxyl radicals which mediate oxidative damage (Yamauchi et al., 1989; Zimmerman et al., 1989; old, 1988). The mechanisms responsible for generation of these free radicals are unknown.

TNF-α enhances the tumoricidal activity of ionizing radiation in vitro and in vivo (Hallahan et al., 1990; Sersa et al., 1988; Wong et al., 1991). The recent combination of TNF-α and radiotherapy in a clinical trial has produced encouraging results (Hallahan et al., 1993). However, toxicity from systemic delivery of TNF-α resulted in fever, nausea, loss of appetite, fatigue, lassitude, and hypotension. TNF-α has been selected as the prototype for gene therapy with radiation because this cytokine is reported to have a radiosensitizing effect in tumor cells and either no effect or a radioprotective effect on normal cells. (Hallahan et al., 1990; Sersa et al., 1988; Wong et al., 1991; Hallahan et al., 1993; Neta et al., 1991).

TNF has been shown to signal a variety of responses including cytotoxicity, vascular changes, anti-viral activity, immunoregulation, and the transcriptional activation of genes that participate in homeostasis and inflammation. TNF was first recognized for it's ability to induce hemorrhagic necrosis in murine tumors. In addition to the effects of TNF on the tumor vasculature and the cellular immune response, TNF is directly cytotoxic to some tumor cells following binding to TNF receptors. The 55 kd TNF receptor initiates a signal cascade which results in cell death. DNA fragmentation and subsequent cell death from TNF is associated with the production of free radicals such as nitric oxide. TNF cytotoxicity is abolished by the radical scavengers (N-acetyl-cysteine, glutathione and DMSO), anoxia, and the enzyme Mn-superoxide dismutase. Recent data has demonstrated that apoptosis is a mechanism of cell killing by TNF, as well as radiation. DNA is cleaved by endonucleases at internucleosomal linker regions resulting in fragments of multiples of 180 base pairs, and DNA fragmentation precedes cell death (Wright, 1992).

TNF interacts with radiation to enhance killing in some human tumor cells. Synergistic (as defined by decrease in $D_0$) or additive killing between TNF- and x-irradiation was observed in 7 human tumor cell lines. Maximal interactive killing effects between TNF- and x-irradiation were observed when TNF- was added 12 to 4 hrs prior to irradiation. However, interactive effects were absent when TNF- was added after irradiation (Hallahan, 1989, Hallahan, 1990). This synergistic effect is observed in a variety of human tumor cells at a dose that is 10% of that required for cytotoxicity (Hallahan, 1989, Hallahan, 1990). Intracellular reactive oxygen intermediate production has been implicated in tumor cell killing by both TNF and radiation. One other possible means of interactive killing by these two agents is through apoptosis which occurs following exposure of some cells to TNF or radiation. These data indicate that these agents may interact synergistically to kill tumor cells.

TNF-α has been added to cell culture media and the cultured cells exposed to x-rays. Where the target tumor cells exist in proximity to non-targeted cells (e.g., non-tumor cells), the delivery of TNF-α to the target cells will also expose non-targeted cells to that cytotoxin. The problem of non-selective toxicity is even more problematic where the target tumor cells are situated in vivo. The systemic delivery of a cytotoxin results in the exposure of virtually all body cells to that toxin.

Combining TNF with radiation might improve the therapeutic ratio because radiosensitization by TNF is possibly limited to tumor cells. Moreover, TNF radioprotects hematopoietic progenitor cells (Ainsworth, 1959). Exogenous TNF added prior to irradiation has also been demonstrated to protect the hematopoietic system in animals (Sersa, 1988, Neta, 1988). TNF may induce radioprotection through the production of manganese superoxide dismutase (MnSOD), which is associated with enhanced bioreduction of radical oxygen species (Wong, 1988, Wong, 1991). These studies further indicate that TNF may improve the therapeutic ratio when administered during radiotherapy.

In view of the above there exists a need in the art for enhancing the toxic effects of radiation on tumor cells while at the same time minimizing any adverse secondary effects of radiation on non-tumor, non-targeted cells.

SUMMARY OF THE INVENTION

The invention relates generally to a process of sensitizing cells to, or protecting cells from, the effects of ionizing radiation. In accordance with this process, cells are transfected with a genetic construct comprising a structural gene encoding a toxin, preferably tumor necrosis factor-α, or a gene for a radioprotector, operatively linked to a constitutive promoter. Any constitutive promoter may be used, as long as its use results in constitutive expression of the toxin gene.

Tumor Necrosis Factor (TNF) has been shown to enhance x-ray killing of human tumor cells in vitro (Hallahan, 1990). To determine the toxicities and efficacy of TNF given prior to radiotherapy, the inventors conducted phase I, dose escalation studies combining these agents. Recombinant human TNF (Knoll Pharmaceutical) was administered systemically 4 hours prior to radiation therapy on consecutive days for a minimum of 2 weeks. Radiation was prescribed to localized fields using dose fractions ranging from 150 to 300 cGy/day for palliation or control of locally advanced disease. Thirty one patients were entered including 16 patients with locally advanced primaries and 15 patients with metastatic sites including liver (7) and bone (3). Major toxicities requiring withdrawal from the study were independent of TNF dose and occurred in 7 patients. These toxicities included hypotension (1) respiratory distress (1), angina (2), atrial fibrillation (1), allergic reaction (1), progressive leukopenia (1). Response to treatment was evaluable in 20 patients. Complete regression (CR) within the field of irradiation was achieved in 4 (cholangiocarcinoma, anaplastic thyroid, melanoma, lung), partial regression (4), minimal regression (5) stable disease (3) and progression of disease (4). A trend toward a greater response rate at higher doses of TNF was observed. Durability of palliation beyond 6 months was achieved in 12/14 patients. Of those patients with locally advanced disease, 4/6 are without progression within the field of irradiation beyond 12 months from completion of treatment (lung (2), cholangiocarcinoma, sarcoma). TNF combined with radiotherapy is no more toxic than TNF alone and may prove to be efficacious in certain malignancies when given at higher concentrations or administered locally.

In one aspect, the present invention relates to a synthetic DNA molecule comprising a constitutive promoter operatively linked to an encoding region that encodes at least one polypeptide, which encoding region is operatively linked to a transcription-terminating region.

In one preferred embodiment, an encoding region encodes a single polypeptide. A preferred polypeptide encoded by such an encoding region is a radiosensitizing factor that has the ability to inhibit the growth of a cell and, particularly a tumor cell.

An exemplary and preferred polypeptide is a cytokine, and more particularly, TNF-α, or IL-1. Other polypeptides that are within the scope of the invention include, but are not limited to a dominant negative or a tumor suppressing factor such as p53, the retinoblastoma gene product, or the Wilms' tumor gene product.

Another preferred polypeptide encoded by such an encoding region has radioprotective activity toward normal tissue. An exemplary and preferred such polypeptide having radioprotective activity is interleukin-1, TNF, bFGF, interleukin-6, a free radical scavenger (MnSOD) or a tissue growth factor receptor.

A further preferred polypeptide encoded by such an encoding region has the ability to catalyze the conversion of a pro-drug to a drug. Exemplary and preferred such polypeptides are herpes simplex virus thymidine kinase and a cytosine deaminase.

The polypeptides of the present invention are able to radiosensitize or radioprotect cells, however, it is recognized that while in some embodiments they interact directly with ionizing radiation to produce the desired effect, in other embodiments these polypeptides do not interact directly with x-irradiation, having their effect on the cell through other means.

In another aspect, the present invention delineates a process of regulating the expression of a polypeptide comprising the steps of first, operatively linking a constitutive promoter to an encoding region that encodes the polypeptide, which encoding region is operatively linked to a transcription-terminating region to form a genetic construct, second, utilizing a viral or liposomal transfer means to deliver the construct to target cells, and finally, exposing the cells to an effective dose of ionizing radiation.

As used herein, an effective dose of ionizing radiation means that dose of ionizing radiation that is generally less than that needed to cause cell damage or death directly, yet interacts with the expressed polypeptides described herein to cause cell damage or death. In embodiments where the genetic construct encodes a radioprotective polypeptide, the effective dose is that which causes damage to unprotected cells, but not to the cells expressing the radioprotective polypeptide. Means for determining an effective amount of radiation are well known in the art. The amount of ionizing radiation needed in a given cell depends inter alia upon the nature of that cell.

By "transfection," of a cell, it is meant to introduce cloned DNA or recombinant vectors into mammalian cells. Examples of transfection procedures include, but are not limited to, the use of calcium phosphate or DEAE-dextran, polybrene, protoplast fusion, electroporation, liposomes, direct microinjection, viral vectors, direct contacting, or direct injection.

In a preferred embodiment an effective expression inducing amount is from about 2 to about 20 Gray (Gy) administered at a rate of from about 0.5 to about 2 Gy/minute. Even more preferably, an effective expression inducing amount of ionizing radiation is from about 5 to about 15 Gy.

As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

Any suitable means for delivering radiation to a tissue may be employed in the present invention. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

Cells containing a DNA molecule of the present invention encoding a particular polypeptide express that polypeptide constitutively, and the polypeptide is able to confer radiosensitization or radioprotection to the cell.

To enhance tumor killing by radiation and to circumvent the problem of systemic toxicity associated with the combination of TNF-α and radiation therapy, the present invention uses gene therapy specifically enhanced by ionizing radiation. In this concept, a construct containing a constitutive promoter upstream to a cDNA encoding a toxin or radioprotector is transcriptionally active within the irradiated field to enhance radiation killing of tumor or to protect normal tissues. Minimal systemic toxicity is anticipated because toxin production is localized in the tumor due to targeting the tumor with a specific delivery vehicle containing the construct.

As used herein, any means of delivering the DNA or construct may be used, including liposome, viral delivery vehicles and cell based systems such as tumor infiltrating lymphocytes being most preferred. This allows targeting of the construct to cells with high specificity and efficiency.

The ability of viruses to enter a cell and express its genetic material in the host cell raises the possibility of replacing lost or defective gene function in vivo. For gene therapy to succeed, there is a need for vectors with the properties of high therapeutic index, large capacity, targeted gene delivery, and tissue-specific gene expression. High therapeutic index indicates high therapeutic effect with low adverse effect, or in other words, a high rate of cure or improvement of the disorder with low or no side effects. This is a pharmacological concept that applies to all therapeutic agents, including gene therapy vectors. However, currently available gene transfer vectors are not able to meet the requirement of high therapeutic index (Mulligan, 1993), because of the vector-borne cyto- or geno-toxicities that are associated with many of the current gene transfer vectors.

Adenoviruses have been widely studied and well-characterized as a model system for eukaryotic gene expression. Adenoviruses are easy to grow and manipulate, and they exhibit broad host range in vitro and in vivo. This group of viruses can be obtained in high titers, e.g., $10^9$-$10^{11}$ plaque-forming unit (PFU)/ml, and they are highly infective. The life cycle of Adenoviruses does not require integration into the host cell genome. The foreign genes delivered by Adenovirus vectors are expressed episomally, and therefore, have low genotoxicity to host cells. Adenoviruses appear to be linked only to relatively mild diseases, since there is no known association of human malignancies with Adenovirus infection. Moreover, no side effects have been reported in studies of vaccination with wild-type Adenovirus (Couch et al., 1963; Top et al., 1971), demonstrating their safety and therapeutic potential as in vivo gene transfer vectors.

Adenovirus vectors have been successfully used in eukaryotic gene expression (Levrero et al., 1991; Gomez-Foix et al., 1992) and vaccine development (Grunhaus and Horwitz, 1992; Graham and Prevec, 1992). Recently, animal studies demonstrated that recombinant Adenoviruses could be used for gene therapy (Stratford-Perricaudet and Perricaudet, 1991; Stratford-Perricaudet et al., 1990; Rich et al., 1993). Successful experiments in administering recombinant Adenovirus to different tissues include trachea instillation (Rosenfeld et al., 1991; Rosenfeld et al., 1992), muscle injection (Ragot et al., 1993), peripheral intravenous injection (Herz and Gerard, 1993), and stereotactic inoculation into the brain (Le Gal La Salle et al., 1993).

Generation and propagation of the current Adenovirus vectors depend on a unique helper cell line, 293, which was transformed from human embryonic kidney cells by AD5 DNA fragments and constitutively expresses E1 proteins (Graham, et al., 1977). Since the E3 region is dispensable from the Adenovirus genome (Jones and Shenk, 1978), the current Adenovirus vectors, with the help of 293 cells, carry foreign DNA in either the E1, the E3 or both regions (Graham and Prevec, 1991). In nature, Adenovirus can package approximately 105% of the wild-type genome (Ghosh-Choudhury, et al., 1987), providing capacity for about 2 extra kb of DNA. Combined with the approximately 5.5 kb of DNA that is replaceable in the E1 and E3 regions, the maximum capacity of the current Adenovirus vector is under 7.5 kb, or about 15% of the total length of the vector. More than 80% of the Adenovirus viral genome remains in the vector backbone and is the source of vector-borne cytotoxicity.

As used herein, the term "recombinant" cell is intended to refer to a cell into which a recombinant gene, such as a gene from the adenoviral genome has been introduced. Therefore, recombinant cells are distinguishable from naturally occurring cells which do not contain a recombinantly introduced gene. Recombinant cells are thus cells having a gene or genes introduced through the hand of man. Within the present disclosure, the recombinantly introduced genes encode radiation sensitizing or radiation protecting factors and are inserted in the E1 or E3 region of the adenovirus genome. It is recognized that the present invention also encompasses genes that are inserted into other regions of the adenovirus genome, for example the E2 region.

It is understood that the adenovirus vector construct may therefore, comprise at least 10 kb or at least 20 kb or even about 30 kb of heterologous DNA and still replicate in a helper cell. By "replicate in a helper cell," it is meant that the vector encodes all the necessary cis elements for replication of the vector DNA, expression of the viral coat structural proteins, packaging of the replicated DNA into the viral capsid and cell lysis, and further that the trans elements are provided by the helper cell DNA. Replication is determined by contacting a layer of uninfected cells with virus particles and incubating said cells. The formation of viral plaques, or cell free areas in the cell layers is indicative of viral replication. These techniques are well known and routinely practiced in the art. It is understood that the adenoviral DNA that stably resides in the helper cell may comprise a viral vector such as an Herpes Simplex virus vector, or it may comprise a plasmid or any other form of episomal DNA that is stable, non-cytotoxic and replicates in the helper cell.

By heterologous DNA is meant DNA derived from a source other than the adenovirus genome which provides the backbone for the vector. This heterologous DNA may be derived from a prokaryotic or a eukaryotic source such as a bacterium, a virus, a yeast, a plant or animal. The heterologous DNA may also be derived from more than one source. For instance, a promoter may be derived from a virus and may control the expression of a structural gene from a different source such as a mammal. Preferred promoters include viral promoters such as the SV40 late promoter from simian virus 40, the Baculovirus polyhedron enhancer/promoter element, RSV, Herpes Simplex Virus thymidine kinase (HSV tk), the immediate early promoter from cytomegalovirus (CMV) and various retroviral promoters including LTR elements.

The promoters and enhancers that comprise the heterologous DNA will be those that control the transcription of protein encoding genes in mammalian cells may be composed of multiple genetic elements. The term promoter, as used herein refers to a group of transcriptional control modules that are clustered around the initiation site for RNA polymerase II. Promoters are believed to be composed of discrete functional modules, each comprising approximately 7-20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. Depending on the promoter, it appears that individual elements can function either cooperatively or independently to activate transcription.

The heterologous DNA of the present invention may also comprise an enhancer. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization.

Taken together, these considerations suggest that enhancers and promoters are homologous entities and that the transcriptional activator proteins bound to these sequences may interact with the cellular transcriptional machinery in fundamentally the same way. It is understood that any such promoter or promoter/enhancer combination may be included in the heterologous DNA of the adenoviral vector to control expression of the heterologous gene regions.

The heterologous DNA may include more than one structural gene under the control of the same or different promoters. The heterologous DNA may also include ribosome binding sites and polyadenylation sites or any necessary elements for the expression of the DNA in a eukaryotic or a mammalian cell. These vector constructs are created by methods well known and routinely practiced in the art such as restriction enzyme digestion followed by DNA ligase directed splicing of the various genetic elements. The heterologous DNA may further comprise a constitutive promoter. A constitutive promoter is a promoter that exhibits a basal level of activity that is not under environmental control. Some examples of constitutive promoters that may possibly be included as a part of the present invention include, but are not limited to, intermediate-early CMV enhancer/promoter, RSV enhancer/promoter, SV40 early and SV-40 late enhancer/promoter, MMSV LTR, SFFV enhancer/promoter, EBV origin of replication, or the Egr enhancer/promoter. However, it is understood that any constitutive promoter may be used in the practice of the invention and all such promoters/enhancers would fall within the spirit and scope of the claimed invention.

Another type of promoter that may comprise a portion of the heterologous DNA is a tissue specific promoter. A tissue specific promoter is a promoter that is active preferentially in a cell of a particular tissue type, such as in the liver, the muscle, endothelia and the like. Some examples of tissue specific promoters that may be used in the practice of the invention include the RSV promoter to be expressed in the liver or the surfactin promoter to be expressed in the lung, with the muscle creatine kinase enhancer combined with the human cytomegalovirus immediate early promoter being the most preferred for expression in muscle tissue, for example.

The cellular exposure to ionizing radiation is associated with transcriptional activation of certain immediate early genes that encode transcription factors (Weichselbaum et al., 1991). These genes include members of the jun-fos, NF-kB and early growth response (EGR-1) gene families (Hallahan et al., 1992; Datta et al., 1992; Brach et al., 1991). The induction of these genes following x-irradiation may represent cellular responses to oxidative stress (Datta et al., 1992; Brach et al., 1991; Datta et al., 1993). Previous studies have demonstrated that induction of Egr-1 gene transcription is mediated by activation of CC(A+T rich)$_6$GG(CArG) motifs in the Egr-1 promoter (Datta et al., 1993; Datta et al., 1992).

When the Egr-1 promoter of the present invention is operatively linked to the gene encoding TNF-α and transfected into cells by HSV-1, however, TNF-α is constitutively expressed.

In certain embodiments, the present invention is a method of expressing a foreign gene in a mammalian cell. This method would comprise the steps of obtaining an adenoviral vector construct comprising more than 7.5 kb of heterologous DNA, replicating the adenoviral vector construct in a helper cell, obtaining virion particles produced by the helper cells and infecting mammalian cells with the virion particles.

The foreign gene to be expressed as described in the preceding paragraph may of any origin, for example, a bacterium, a yeast, a plant, an animal or even a human gene.

Preferably the adenovirus vector construct contains a deletion in the E1 or E3 region of the genome and the foreign gene is inserted in its place.

The virion plaques that would be produced by the replicating viral vector and would thus lyse the host cell can be obtained by any acceptable means. Such means would include filtration, centrifugation or preferably physical touching of viral plaques. All such methods of obtaining virion particles and infecting mammalian cells with the particles are well known to those of skill in the art.

The examples of preferred embodiments disclosed herein utilize human adenovirus type 5. Type 5 virus was selected because a great deal of biochemical and genetic information about the virus is known, and it has historically been used for most constructions employing adenovirus as a vector. It is understood, however, the adenovirus may be of any of the 42 different known serotypes of subgroups A-F. Adenovirus type 5 of subgroup C is the preferred starting material in order to obtain the conditional replication-defective adenovirus vector for use in the method of the present invention.

Any of a large number of promoters may be used to direct expression of the TNF-α gene. In the examples given, the human cytomegalovirus (CMV) immediate early gene promoter has been used (Thomsen et al., 1984), which results in the constitutive, high-level expression of the foreign gene. However, the use of other viral or mammalian cellular promoters which are well-known in the art is also suitable to achieve expression of TNF-α, provided that the levels of expression are sufficient to achieve a physiologic effect.

By employing a promoter with well-known properties, the level and pattern of expression of TNF-α following infection can be optimized. For example, selection of a promoter which is active specifically in certain cell types will permit tissue-specific expression of the TNF-α.

In still further embodiments, the invention relates to a method for increasing TNF-α levels in a subject comprising administering to the subject an effective amount of a pharmaceutical composition which includes the adenovirus vector/TNF-α construct. The inventors propose that an effective amount of the vector construct will involve the administration of from about $10^8$ to $10^{11}$ virus particles, which may be given either as a single bolus injection directly into the tumor or as a systemic intravenous infusion over several hours.

Other than the requirement that the adenovirus vector be replication defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the method of the present invention. This is because Adenovirus type 5 is a human adenovirus of which a great deal of biochemical and genetic information is known, and it has historically been used for most constructions employing adenovirus as a vector.

In further embodiments, the invention relates to pharmaceutical compositions wherein the adenovirus vector/TNF-α gene construct is dispersed in a pharmacologically acceptable solution or buffer. Preferred solutions include neutral saline solutions buffered with phosphate, lactate, or Tris, containing sucrose or glycerol, and the like. Of course, one will desire to purify the vector sufficiently to render it essentially free of undesirable contaminant, such as defective interfering adenovirus particles or endotoxins and other pyrogens such that it will not cause any untoward reactions in the individual receiving the vector construct. A preferred means of purifying the vector involves the use of buoyant density gradients, such as cesium chloride gradient centrifugation.

In that adenovirus is a virus that infects humans, there may be certain individuals that have developed antibodies to certain adenovirus proteins. In these circumstances, it is possible that such individuals might develop an immunological reaction to the virus. Thus, where an immunological reaction is believed to be a possibility, one may desire to first test the subject to determine the existence of antibodies. Such a test could be performed in a variety of accepted manners, for example, through a simple skin test or through a test of the circulating blood levels of adenovirus-neutralizing antibodies. In fact, under such circumstances, one may desire to introduce a test dose of on the order of $1 \times 10^5$ to $1 \times 10^6$ or so virus particles. Then, if no untoward reaction is seen, the dose may be elevated over a period of time until the desired dosage is reached, such as through the administration of incremental dosages of approximately an order of magnitude.

The particular cell line used to propagate the recombinant adenoviruses of the present invention is not critical to the present invention. The recombinant adenovirus vectors can be propagated on, e.g., human 293 cells, or in other cell lines that are permissive for conditional replication-defective adenovirus infection, e.g., those which express adenovirus E1A gene products "in trans" so as to complement the defect in a conditional replication-defective vector. Further, the cells can be propagated either on plastic dishes or in suspension culture, in order to obtain virus stocks thereof.

Liposomes have been used for more than 10 years for the introduction of exogenous DNA into cells (Mukherjee et al., 1978) and for 7 years in animals (Nicolau et al., 1983). The term liposome is used to describe different forms of surfactant vesicles consisting of one or more concentric lipid bilayer spheroids surrounding an aqueous space. Classical liposomes consist of fatty acid esters and fat-alcohol ethers of glycerol phosphatides. Their net charge is negative under physiological pH conditions due to phosphate groups. In recent years, liposomes bearing a positive charge derived from quaternary ammonium groups such as N-(1-(2,3-dioleoyloxy)propyl)-N,N,N-trimethylammonium chloride (DOTMA)$^2$ (Felgner et al., 1987) have been introduced. These cationic liposomes interact strongly with cellular membrane which are themselves negatively charged. In contrast to classic liposomes they do not encapsulate or entrap DNA but bind it at their surface. Another group of liposomes consists of nonionic surfactant vesicles. While classical phospholipid-based liposomes are of low toxicity, the toxicity and antigenicity of the partially synthetic cationic and nonionic liposomes have not been rigorously evaluated.

As used herein, exemplary liposome preparations include, but are not limited to DOTMA, 1,2-dioleyloxypropyl-3-trimethyl ammonium bromide; DOPE, dioleoylphosphatidylethanolamine; POPE, palmitoyloleoylphosphatidylethanolamine; DMPE, dimyristoylphosphatidylethanolamine; DPPE, dipalmitoylphosphatidylethanolamine; DSPE, distearoylphosphatidylethanolamine; PMME, dioleoylphosphatidylmonomethylethanolamine; PDME, dioleoylphosphatidyldimethylethanolamine; DOPC, dioleoylphosphatidylcholine; CPE, dioleoylphosphatidylcaprylamine; DPE, dioleoylphosphaqtidyldodecylamine; DORI, 1,2-dioleoyl-3-dimethyl-hydroxyethyl ammonium bromide (Dioleoyl Rosenthal Inhibitor); or DORIE, 1,2-dioleyloxypropyl-3-dimethyl-hydroxyethyl ammonium bromide;

The present invention also embodies a method using HSV-1 for delivering genes for gene therapy. In an exemplary embodiment, the method involves combining the gene used for gene therapy with the HSV-1 virus rendered non-pathogenic. The gene and the virus are then combined with a pharmacologically acceptable carrier in order to form a pharmaceutical composition. This pharmaceutical composition is then administered in such a way that the mutated virus containing the gene for therapy, or the HSV-1 wild type virus containing the gene, can be incorporated into cells at an appropriate area. The use of the HSV-1 virus with a specific mutation in the $\gamma_1 34.5$ gene provides a method of therapeutic treatment of tumorigenic diseases both in the CNS and in all other parts of the body (Chou 1992). The "$\gamma_1 34.5$ minus" virus can induce apoptosis and thereby cause the death of the host cell, but this virus cannot replicate and spread (Chou 1992). Therefore, given the ability to target tumors within the CNS, the $\gamma_1 34.5$ minus virus has proven a powerful therapeutic agent for hitherto virtually untreatable forms of CNS cancer. Furthermore, use of substances, other than a virus, which inhibit or block expression of genes with anti-apoptotic effects in target tumor cells can also serve as a significant development in tumor therapy and in the treatment of herpes virus infection, as well as treatment of infection by other viruses whose neurovirulence is dependent upon an interference with the host cells' programmed cell death mechanisms. The procedures to generate the above recombinant viruses are those published by Post and Roizman (1981), and U.S. Pat. No. 4,769,331, incorporated herein by reference.

Retroviruses may also be used to deliver the constructs to the host target tissues. These viruses in which the 3' LTR (linear transfer region) has been inactivated. They are enhancerless 3'LTR's, often referred to as self-inactivating viruses because after productive infection into the host cell, the 3'LTR is transferred to the 5' end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell A search for more potent cells to use in adoptive immunotherapy led to the description of TIL, cells that recognize unique antigens in murine and human tumors in a major, histocompatibility complex-restricted fashion. The adoptive transfer of TIL was from 50- to 100-fold more potent than that of LAK cells in animal therapy models. In the initial clinical trials with TIL, objective response rates of 35% to 40% occurred in patients with malignant melanoma. The response rates to TIL were almost twice those obtained with IL-2 alone or LAK cells plus IL-2. Studies with indium-111-labeled TIL injected intravenously into patients with cancer demonstrated that these cells traveled to and accumulated in tumor deposits. These studies suggested that TIL might be used as vehicles for delivering molecules to tumor sites that could aid in the antitumor effectiveness of TIL. The inventors propose to use TIL and other cell based systems to deliver to deliver diffusible radiosensitizing or radioprotecting genes to tissues prior to irradiation (e.g. TNF).

There are several potential advantages of employing constitutive promoters in genetic constructs with therapeutic radiation treatment. One advantage is that multiple radiation doses (20-35 daily treatments) are usually employed in a treatment course of radiotherapy. Therefore, a small increment in cell killing per treatment might increase the therapeutic index because the increase in tumor cell killing is magnified by an exponent equal to the number of treatments. Many types of localized tumors are amenable to multiple installations of radiation inducible genetic constructs. Additionally, the already well-developed technology of radiation targeting in combination with the localization of constitutive toxin production provides a novel and surprisingly synergistic enhancement of tumor cell killing or radioprotection of normal tissues to tumor therapy.

The invention also concerns methods of in vitro testing to assess the responses of different cells to selected radiosensitizing or radioprotecting factors, determining if the cells respond to that particular factor and the radiation dose in a synergistic or additive manner. A particular advantage of this method is that it allows the skilled artisan and clinician to make choices relating to the selection of radiosensitizing or radioprotective agents to use in treatment protocols, based on the cell type to be treated.

Studying the effects of such protocols on tumor cells in vitro is an effective means by which to assess the effectiveness of these new treatment methods. Model systems to assess the killing of transformed (cancerous) cells are known to be predictive of success in human treatment regimens, partly as the cell types are essentially the same and all malignant cells simply proliferate, having little interaction with other systems. This is different from the problems found using other more interactive biological systems, such as, for example, when studying components of the immune system in isolation.

Other models designed to allow optimization of these methods will naturally be employed prior to translating to a clinical environment. In particular, one may assess the effects in various animal model systems of cancer, including those in which human cancer cells are localized within an animal.

In another aspect, the present invention contemplates a pharmaceutical composition comprising a therapeutically effective amount of at least one genetic construct of the present invention and a physiologically acceptable carrier.

A therapeutically effective amount of a genetic construct that is combined with a carrier to produce a single dosage form varies depending upon the host treated and the particular mode of administration.

As is well known in the art, a specific dose level for any particular patient depends upon a variety of factors including the activity of the specific compound employed, the age, body weight, general health, sex, diet, time of administration, route of administration, rate of excretion, drug combination, and the severity of the particular disease undergoing therapy.

A composition of the present invention is typically administered orally or parenterally in dosage unit formulations containing standard, well known nontoxic physiologically acceptable carriers, adjuvants, and vehicles as desired. The term parenteral as used herein includes subcutaneous injections, intravenous, intramuscular, intraarterial injection, or infusion techniques.

Injectable preparations, for example, sterile injectable aqueous or oleaginous suspensions are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

A genetic construct of the present invention can also be complexed with a poly(L-Lysine) (PLL)-protein conjugate such as a transferrin-PLL conjugate or an asialoorosomucoid-PLL conjugate.

Liquid dosage forms for oral administration include pharmaceutically acceptable emulsions, syrups, solutions, suspensions, and elixirs containing inert diluents commonly used in the art, such as water. Such compositions can also comprise adjuvants, such as wetting agents, emulsifying and suspending agents, and sweetening, flavoring, and perfuming agents.

The combination of radiation treatment and a constitutive promoter linked to TNF-α cDNA in an ex vivo gene delivery system produces tumor cures which are greater than those produced by treatment with either modality alone. Cells that contain genetic constructs constitutively producing toxins and are targeted with ionizing radiation provides a new conceptual basis for increasing the therapeutic ratio in cancer treatment.

DETAILED DESCRIPTION OF THE PREFERRED EMBODIMENTS

The present invention relates generally to the preparation and use of nucleic acid constructs containing a constitutive promoter operatively linked to a cDNA for a toxin that are delivered to the tumor site prior to radiation treatment as a means of enhancing cell killing in the radiation field. To minimize the effects of toxins systemically applied to an organism, the constructs are delivered to tumors or other tissues prior to radiation treatment by using viral or liposomal delivery vehicles. In addition to delivering the toxin gene or radioprotector gene to the cells to be treated by radiation, the delivery vehicles themselves may contribute to cell killing, acting in a synergistic manner in concert with radiation and the toxin gene carried into the cell.

Adenovirus is particularly suitable for use as a gene transfer vector because of its mid-sized genome, ease of manipulation, high titer, wide target-cell range, and high infectivity. Adenoviruses are double-stranded DNA viruses with a linear genome of approximately 36 kb. Both ends of the viral genome contain 100-200 base pair (bp) inverted terminal repeats (ITR), which are cis elements necessary for viral DNA replication and packaging. The early (E) and late (L) regions of the genome that contain different transcription units are divided by the onset of viral DNA replication.

It is known that a part of the adenoviral genome can be replaced by foreign DNA and the virus can still replicate in helper cells that supply the proteins encoded by the displaced viral genome in trans. The currently available Adenovirus vectors carry foreign DNA in either early region 1 (E1) or 3 (E3) or both, and are replicated primarily in the 293 cell line, a transformed human embryonic kidney cell line that constitutively expresses E1 proteins (Graham et al., 1977; Graham and Prevec, 1991). However, the recombinant DNA capacities of the vectors generated in this system are limited to 7.5 kb.

Introduction of foreign genes into somatic cells in intact animals has been achieved with a variety of vectors, including recombinant retroviruses, synthetic vectors and recombinant adenoviruses (reviewed in Berkner, 1988; Miller, 1992; Anderson, 1992; Gerard et al., 1993), and in some cases expression of cellular proteins or paracrine growth factors has been sufficiently efficient to produce demonstrable physiologic effects. In vivo somatic cell gene transfer to produce physiologically meaningful quantities of a serum protein, however, has not been previously demonstrated. The embodiments of the present invention described herein demonstrate that adenovirus mediated gene transfer results in significant overexpression of TNF-α in tissues.

As shown in the studies set forth below, the CMV promoter is employed to drive expression of the inserted genes. However, it is contemplated that other promoters may be successfully employed where desired, such as the Rous sarcoma virus long terminal repeat (RSV-LTR) that was employed by Jaffe et al. (1992). One will prefer to employ a strong promoter such as the CMV promoter for the practice of the invention because a high expression level in tissues is important. In general, it is believed that any constitutive promoter may be employed, so long as it is sufficiently strong to promote a physiologic effect. Exemplary promoters include, but are not limited to, the β-actin promoter, the $\alpha_1$-antitrypsin promoter, the PA1-1 promoter, intermediate-early CMV enhancer/promoter, RSV enhancer-promoter, SV40 early and SV-40 late enhancer/promoter, MMSV LTR, SFFV enhancer/promoter, EBV origin of replication, actin, Egr enhancer/promoter and the like.

The inventors have shown that recombinant adenovirus, herpes simplex virus, or liposomes can be used to efficiently transfer an exogenous gene like TNF-α to cells. Gene expression can be influenced by the number of virus particles contacted to the cells, a property that is desirable for clinical application of somatic gene therapy.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Production of TNF-α Before and During X-Irradiation

The following specific methods were used in Example 1.

Cell Lines. Methods of establishment of human sarcoma and epithelial cell lines have been described (Weichselbaum, et al., 1986; 1988). Culture medium for epithelial tumor cells was 72.5% Dulbecco's modified Eagle's medium/22.5% Ham's nutrient mixture F-12 (DMEM/F-12 (3:1))$_5$% fetal bovine serum (FBS), transferrin at 5 µg/ml/$10^{-10}$ M cholera toxin/$1.8 \times 10^{-4}$ M adenine, hydrocortisone at 0.4 µg/ml/2× $10^{-11}$ M tri-iodo-L-thyronine/penicillin at 100 units/ml/ streptomycin at 100 µg/ml. Culture medium for sarcoma cells was DMEM/F-12 (3:1)/20% FBS, penicillin at 100 units/ml/ streptomycin at 100 µg/ml.

TNF-α Protein Assay. Human sarcoma cells were cultured as described above and grown to confluence. The medium was analyzed for TNF-α 3 days after feeding and again 1-3 days after irradiation. Thirteen established human sarcoma cell lines were irradiated with 500-centigray (cGy) x-rays with a 250-kV Maxitron generator (Weichselbaum, et al., 1988). TNF-α was measured by ELISA with two monoclonal antibodies that had distinct epitopes for TNF-α protein (Sariban, et al., 1988); the assay detects TNF-α from 0.1 to 2.0 units/ml.

TNF-α ELISA Assay

Collection of Samples and Storage

Cell Culture Supernates—Centrifuge to remove any particulate material and stores at −20° C. Avoid freeze thaw cycles.

Serum—Use a serum separator tube (SST) or allow samples to coagulate in the refrigerator and centrifuge. A rapid separation of serum after coagulation, less than 30 minute, ensures optimal recovery. Aspirate serum and assay. Samples may be stored frozen at ≦20° C. Avoid freeze thaw cycles.

Plasma—Collect plasma using EDTA, heparin, or citrate as anticoagulant. A rapid separation of plasma after collection, less than 30 minute, ensures optimal recovery. If using citrate or heparin collection tubes, make sure they are pyrogen-free to avoid endogenous TNF-α production. Remove particulates by centrifugation and assay. Samples may be stored frozen at ≦−20° C. Avoid freeze thaw cycles.

Reagent Preparation

Bring all reagents to room temperature before use.

Wash Buffer—Dilute 20 mL of Wash Buffer Concentrate into deionized or distilled water to prepare 500 mL of Wash Buffer. Store for up to 30 days at 2-8° C. Any precipitate formed during storage will redissolve upon dilution. If a precipitate has formed, mix the concentrate well before diluting.

Substrate Solution—Color Reagents A and B should be mixed together in equal volumes within 15 minutes of use. 200 µL of the resultant mixture is required per well.

TNF-α Standard—It is important that the diluent selected for reconstitution and dilution of the standard reflect the environment of the samples being measured. If available, a diluent identical to the samples should be used. If not, Calibrator Diluent RD5 (R&D Systems) will be suitable for many applications, including measurements made in most culture media. Calibrator Diluent RD6 is serum based and may be used when serum/plasma samples are being tested.

Reconstitute the TNF-α Standard with 1 mL of deionized water (for culture media samples), Calibrator Diluent RD6 (for serum/plasma samples), or a diluent that reflects the composition of the samples being assayed. This reconstitution produces a stock solution of 1000 pg/mL. Allow the standard to sit for a minimum of 15 minutes with gentle agitation prior to making dilutions. Use this stock solution to produce a dilution series, as described on the following page, within the range of this assay (15.6 pg/mL to 1000 pg/mL).

A suggested dilution series for standards is 1000 pg/mL, 500 pg/mL, 250 pg/mL, 125 pg/mL, 62.5 pg/mL, 31.3 pg/mL, 15.6 pg/mL, and 0 pg/mL. Calibrator Diluent RD5 (culture supernate samples) or RD6 (serum samples) may be used for the dilution series.

1. Label six tubes: 500 pg/mL, 250 pg/mL, 125 pg/mL, 62.5 pg/mL, 31.3 pg/mL, and 15.6 pg/mL. Pipette 0.5 mL of the appropriate diluent into each tube.
2. Pipette 0.5 mL of the 1000 pg/mL TNF-α standard into the 500 pg/mL tube and mix thoroughly.
3. Transfer 0.5 mL from the 500 pg/mL tube to the 250 pg/mL tube and mix thoroughly.
4. Repeat this process successively to complete the 2-fold dilution series.
5. The undiluted TNF-α standard will serve as the high standard (1000 pg/mL).
6. Use the appropriate diluent as the zero standard (0 pg/mL).

Standards may be stored at 2-4° C. for up to 12 hours following reconstitution. Do not use standards that have been reconstituted for more than 12 hours. Discard any remaining reconstituted standards. Avoid freeze thaw cycles; aliquot if repeated use is expected.

Assay Procedure—Bring all reagents and samples to room temperature before use. It is recommended that all samples and standards be assayed in duplicate. Conjugate incubation times differ for non-serum vs. serum and benchtop vs. shaker assays.

Culture Supernate Assay—(3.5 hour benchtop, 2.0 hour shaker assay)
1. Open the resealable foil pouch containing the microtiter plate. Remove any excess microtiter plate strips from the plate frame, return them to the foil pouch, reseal.
2. Add 50 µL of Assay Diluent RD1F to each well.
3. Add 200 µL of standard or sample per well. Cover with the provided adhesive strip and incubate for 2 hours at room temperature on the benchtop. For the shaker assay, incubate 1 hour on the shaker (500 rpm±100 rpm).
4. Aspirate each well and wash, repeating the process three times. Wash by filing each well with Wash Buffer (400 µL) using a squirt bottle, pipette, or manifold dispenser. Complete removal of liquid at each step is essential to good performance. After the last wash, remove any remaining Wash Buffer by inverting the plate and blotting it against clean paper toweling or by aspirating.
5. Add 200 µL of TNF-α Conjugate. Cover with a new adhesive strip and incubate for 1 hour at room temperature on the benchtop. For the shaker assay, incubate 30 minutes on the shaker.

Calculation of Results—Average the duplicate readings for each standard, control, and sample and subtract the average zero standard optical density.

Plot the optical density for the standards versus the concentration of the standards and draw the best curve. The data can be linearized by using log/log paper and regression analysis may be applied to the log transformation.

To determine the TNF-α concentrations for each sample, first find the absorbance value on the y-axis and extend a horizontal line to the standard curve. At the point of intersection, extend a vertical line to the x-axis and read the corresponding TNF-α concentration. If samples have been diluted, the concentration read from the standard curve must be multiplied by the dilution factor.

Typical Data

Any variation in standard diluent, operator, pipetting and washing technique, incubation time or temperature, and kit age can cause variation in binding. The following examples contain data obtained using the RD5 and RD6 diluents.

The following data was obtained for a standard curve using Calibrator Diluent RD5.

| Standard (pg/mL) | O.D. | Average | Zero Standard Subtracted |
| --- | --- | --- | --- |
| 0 | 0.033 | | |
| 0 | 0.035 | 0.034 | |
| 15.6 | 0.073 | | |
| 15.6 | 0.080 | 0.076 | 0.042 |
| 31.3 | 0.125 | | |
| 31.3 | 0.122 | 0.125 | 0.090 |
| 62.5 | 0.199 | | |
| 62.5 | 0.199 | 0.199 | 0.165 |
| 125 | 0.369 | | |
| 125 | 0.369 | 0.369 | 0.335 |

-continued

| Standard (pg/mL) | O.D. | Average | Zero Standard Subtracted |
| --- | --- | --- | --- |
| 250 | 0.679 | | |
| 250 | 0.673 | 0.676 | 0.642 |
| 500 | 1.243 | | |
| 500 | 1.232 | 1.238 | 1.204 |
| 1000 | 2.094 | | |
| 1000 | 2.131 | 2.112 | 2.078 |

Synergistic Killing by X-Irradiation and TNF-α Exponentially growing cells were irradiated by using a 250-kV x-ray generator. The colony-forming assay was used to determine cell survival (Weichselbaum, et al., 1988). The multitarget model survival curves were fit to a single-hit multitarget model ($S=1-(-e^{-D/D_0})^n$). Concentrations of recombinant human TNF-α (10 units/ml) ($2:3\times10^6$ units/mg) and (1000 units/ml) (Asahi Chemical, New York) were added 24 hr before irradiation.

Results

The effect of TNF-α on radiation-induced cytotoxicity in TNF-α-producing cell lines is shown by the addition of recombinant human TNF-α to cultures before irradiation. Recombinant human TNF-α (1000 units/ml) ($2.3\times10^6$ units/mg) was cytotoxic to four of five TNF-α-producing sarcomas (STSAR-5, -13, -33, and -43). The plating efficiency (PE) was reduced by 60-90% at 1000 units/ml in these lines. Radiation-survival analysis of cell line STSAR-33 was performed with TNF-α (10 units/ml). The radiosensitivity ($D_0$), defined as the reciprocal of the terminal slope of the radiation survival curves plotted semi-logarithmically, was 80.4 cGy for cell line STSAR-33. When TNF-α was added 20 hr before irradiation, the $D_0$ was 60.4 cGy. Surviving fractions were corrected for the reduced PE with TNF-α. Thus, the interaction between TNF-α and radiation in STSAR-33 cells has been shown to be synergistic (Dewey, 1989).

Sublethal concentrations of TNF-α (10 units/ml) enhanced killing by radiation in cell line STSAR-33, suggesting a radiosensitizing effect of TNF-α The surviving fraction of cell line STSAR-5 at 100-700 cGy was lower than expected by the independent killing of TNF-α and x-rays, although the $D_0$ values were similar. Thus, the interaction between TNF-α and radiation is additive (Dewey, 1979) in STSAR-5 cells. Cell lines STSAR-13 and STSAR-43 were independently killed with x-rays and TNF-α, and no interaction was observed.

To determine the possible interactions between TNF-α and x-rays in non-TNF-α producing cells, human epithelial tumor cells (SQ-20B and HNSCC-68) were irradiated 20 hr after TNF-α was added. These cell lines do not produce TNF-α in response to ionizing radiation. TNF-α (1000 units/ml) was cytotoxic to SQ-20B and SCC-61 cells, reducing the PE by 60-80%. The $D_0$ for cell line SQ-20B with radiation alone is 239 cGy. With TNF-α (1000 units/ml) added 24 hr before x-rays, the $D_0$ was 130.4 cGy. Therefore, a synergistic interaction (Dewey, 1979) between TNF-α and x-rays was demonstrated in this cell line. TNF-α added after irradiation did not enhance cell killing by radiation in cell lines SQ-20B. Nonlethal concentrations of TNF-α (10 units/ml) resulted in enhanced radiation killing in cell line HNSCC-68, providing evidence that TNF-α may sensitize some epithelial as well as mesenchymal tumor cell lines to radiation.

Example II

TNF-α interacts with radiation to enhance killing in some human tumor cells: Studies were performed on the interaction between recombinant TNF-α and x-irradiation in epithelial and mesenchymal human tumors cell lines. Synergistic (as defined by decrease in $D_0$) or additive killing between TNF-α and x-irradiation was observed in 7 human tumor cell lines. Maximal interactive killing effects between TNF-α and x-irradiation were observed when TNF-α was added 12 to 4 hrs prior to irradiation. However, interactive effects were absent when TNF-α was added after irradiation (67, 68). In studies performed to determine whether apoptosis plays a role in the interactive killing between TNF-α and radiation, SQ-20B cells, which have previously shown an interactive killing between TNF-α and radiation, were treated with 5 ng/ml (5 ng=10 units) TNF-α alone, 5 ng/ml TNF-α 4 hours prior to 10 Gy or 10 Gy alone. The percentage of cells undergoing DNA fragmentation characteristic of apoptosis were quantified by the terminal transferase assay as described in the Methods in Specific Aim 1 (69) after treatment. The determination of the fraction of cells undergoing DNA fragmentation is noted in the vertical axis in FIG. 2. Almost no cells undergo apoptosis at 48 hrs following treatment with TNF-α alone (5 ng/ml) or radiation alone (10 Gy) (FIGS. 2B,C). FIG. 2D shows that at 48 hours, 21% of the cells treated with 5 ng/ml TNF-α and 10 Gy are in the process of fragmenting DNA. These data suggest that TNF-α enhances radiation killing by increasing apoptosis. It is noteworthy that even relatively small increases in apoptosis in a multi-fractionated radiotherapy scheme may have a large effect on the final surviving fraction.

Example III

Usefulness of TNF-α in Radiotherapy

TNF-α has largely been abandoned as a sole therapeutic agent because of toxicity. The inventors' in vitro data suggested that clinically tolerable TNF-α concentrations might interact with radiation and might therefore be effective in clinical radiotherapy without being directly cytotoxic. In a Phase I (toxicity) evaluation study of TNF-α (10-150 μg/m²) and radiotherapy, TNF-α was given 4 hours prior to radiation on consecutive days for a minimum of two weeks. Response to treatment was evaluated in 21 patients with advanced local or metastatic cancer. Complete regression within the radiation fields was achieved in 5 patients and partial regression in another 6 patients. Three patients had a minimal response. Tumor histologies considered clinically radioresistant such as biliary carcinoma, anaplastic thyroid carcinoma, unresectable lung carcinoma, and melanoma were among the patients who achieved complete responses to treatment. Four of six patients with advanced local disease are alive without evidence of disease at 24 months; one additional patient with advanced local disease (a large abdominal soft tissue sarcoma) has stable disease at 24 months. Toxicities from systemic TNF-α delivery included rigors, fevers and hypotension. These results show that while no survivors were expected at 24 months in this group of patients (Hallahan et al. 1993).

Example IV

Preparation of Recombinant Adenovirus-TNF Constructs

Materials and Methods

For cell growth, set up twenty cm plates with 293 cells (ATCC #cr11573): seed cells in complete media and culture at 37° C., 5% $CO_2$ until 70-80% confluent (three 15 cm plates split into 20 plates should be ready to infect in about 3-5 days). Media to be used is IMEM, 10% (v/v) FBS (Heat inactivated: 56° C., 30 min) 2 mM Glutamine, 50 units/ml Penicillin, 50 μg/ml Streptomycin, 1% (w/v) Fungizone (antibiotics are optional). Cell Preparation—Cells Cats: 293 cells must be handled carefully as they are sensitive and quite fragile. Avoid drying—aspirate media only when ready to immediately proceed to infection and avoid cold temperature—always use RT or 37° C. media (never cold, e.g. from the refrigerator) Excessive mechanical manipulation should be avoided since 293 cells detach easily from the dish. Hence, to avoid loosening the cell monolayer, always add media to the side of a tilted dish. Prolonged time out of incubator should be avoided since cells are quite sensitive to changes in pH.

Infection Procedure:

To prepare virus-containing Infection media, first prepare high titer viral stock (preferred source of virus for infection). To do this, first thaw virus quickly at RT and keep on wet ice. Mix virus by pipetting. Next, for each plate, mix the following just prior to use: 10=100 plaque forming units (PFU) recombinant adenovirus/cell (Typically 1-3 μl of high titer stock)+ 1.25 ml Infection media. For a total of twenty plates: typically one would use 20-60 μl virus+26.5 ml media (1.25 ml media extra added to account for volume loss during pipetting).

To prepare a Crude Viral Lysate (CVL, not a preferred source, but occasionally necessary), first, for each plate, mix the following just prior to use: 85 μl CVL+1.25 ml Infection media. For a total of twenty plates: (1.7 ml CVL+25 ml media) Aspirate old media from plates and immediately add the appropriate amount of virus-containing infection media. Note: do not handle more than 5 plates at one time. Incubate plates in a humidified atmosphere for 1.5 hr at 37° C., 5% $CO_2$. Plates should be very slowly and gently rocked with a rocker platform in the tissue culture incubator. Rotate plates 90° every 15 min so that the media covers all parts of the plate. After 90 min, add 20 ml of complete media to each plate and incubate cells (37° C., 5% $CO_2$, humidified atmosphere) until they are ready for the next step.

The cells are ready to be harvested when they show cytopathic effect (CPE; a rounded appearance) and start to detach from the plate in a configuration similar to Staph A "grape clusters". This phenomena starts after 24 hr and is fully developed after 30-36 hr. Within this time range, the cells should be harvested. If CPE is evident before 24 hr, the CPE could be due to effect of viral proteins (sometimes seen with infections using CVL).

Detach the cells by pipetting fluid and cells up and down using a 25 ml pipet (collect all cells because virus is mostly intracellular). Recover cells in sterile, single use polypropylene tubes by centrifugation (clinical tabletop centrifuge, 10 min, 1500 rpm, 4° C.). Resuspend the pellet in supernatant fluid (5 ml total volume). Treat supernatant with chlorine bleach before discarding down the sink because it is biohazardous.

To purify the virus, freeze/thaw 5× to lyse the cells and release the virus. The result is termed crude viral lysate (CVL). Use dry ice and 37° C. bath to cycle through freezing and thawing and vortex between each freeze/thaw cycle. Next, to remove cell debris from CVL, perform low speed centrifugation using 2059 Falcon tubes (Sorvall HS4 rotor, 7000 rpm, 4° C., 5 min). Next, using ultraclear Beckman #344060 ultracentrifuge tubes and a SW40 rotor, centrifuge the supernatant at 7000 rpm, 4° C., 5 min). An aliquot CVL should be saved and frozen at −70° C. (200 μl should be adequate). Recover the supernatant (cleared CVL) and bring to 4.5 ml (for SW41) or 5.2 ml (for SW40) with sterile phosphate buffered saline (PBS).

For final purification of the virus prepare, ultra-clear SW41 (SW40) (Beckman) tubes by soaking in 95% ETOH followed by sterile H$_2$O air dry in the hood (need 2 tubes for each viral preparation).

For the first ultracentrifugation, place low density (1.25 g/ml) CaCl in an ultra-clear tube. Next, underlay high density (1.40 g/ml) CaCl using a sterile 2 ml pipet. This is followed by overlaying cleared CVL (from step #2 above) using a sterile 5 ml pipet. Measure weight accurately using a pan balance in order to have well balanced tubes during the ultracentrifugation. Balance opposing tubes using CaCl and PBS.

Centrifugation is performed in an SW41 rotor/L8M ultracentrifuge: (35,000 rpm, 20° C., 1 hr, acceleration 1, deceleration 4) This is followed by centrifugation in a SW40 rotor/L7-65 ultracentrifuge: (35,000 rpm, 20° C., 1 hr, brake off).

The lower opalescent band containing infectious adenovirus is collected with a 3 ml syringe and 21 ga needle by side puncture. Clean tube with 95% ethanol prior to collection. It is sometimes useful to remove the empty capsid band first when this band is close to the infectious virus band.

A second Ultracentrifugation is performed in a fresh ultraclear tube 8 ml of 1.33 g/ml CsCl. The band recovered from the first centrifugation is then overlayed and centrifuged as above, except for 18 hr. Again, be careful to ensure that the tubes are balanced prior to ultracentrifugation. Weigh tubes and adjust weight to balance using 1.33 g/ml CsCl solution. The opalescent band is recovered as above and placed in a sterile microcentrifuge tube. The bands are kept on ice from now on.

For final purification, dialyze the band against: 10 mM Tris pH 7.4, 1 mM MgCl$_2$, 10% (v/v) Glycerol, recover the virus and aliquot into sterile microcentrifuge tubes. Aliquots should include 15 μl (×4), and ≦100 μl, and are stored at −70° C.

Titering of Adenovirus

To treat cells in culture, first set up 6-well plates with 293 cells-1.5-2.0×10$^6$/well. Next, make up overlay of 2% Sea-Plaque Agarose in Abbott water—boil 3 min. Individual Wrapped Sterile Flask (Corning). Place in 420 water bath. (Store on shelf and reboil 1 min. for next use.) Infection media consists of IMEM, 2% HIFBS and 1% Glu.

Transfection Procedure

First, prepare 1:10 serial dilutions of virus to infection media. To inoculate cells, remove media off one plate at a time. Suck up fast but carefully from side of each well. Next, add 1 ml of infection media slowly onto side of each well (use 5 ml pipette). Immediately add 1000 μl of #11 dilution tube to #11 well; pipette up and down slowly 3 times. Then repeat and add #10 dilution tube to #10 well etc. Tip plate as you do these additions. Rock plates for 90 min in incubator.

Overlay each plate by combining 1:1 2% Seaplaque Agarose (420) and 2×MEM mix (37°) in blue conical. Pipette up and down several times. Wait till temp. is 37° or a little below. Aspirate off carefully the infection media from one plate. With 10 ml pipette add 2 ml overlay mix carefully to side of each well. Place plate in incubator. Overlay again in 5 days, twice more.

Example V

Liposome Preparation

Liposomes used were DOTMA (Boehringer-Mannheim, Mannheim, Germany) and lipofectin (BRL, MD, U.S.A.) preparations. Both preparations follow the strategy of Felgner et al. (Felgner et al., 1987). Lipofectin is an equimolar mixture of DOTMA and dioleoylphosphatidylethanolamine. The concentration of the commercial suspensions are given as 1 mg/ml.

Tumor cell lines SQ20B, Pro4L, and 1591 cells were grown as monolayers, and incubated for 30 min in a volume of 3 ml transfection buffer (HPS buffer; 150 mM NaCl, pH 7.4) 20 mM Hepes, with 10 μg of DNA attached to the necessary amount of carrier particles. After this incubation period medium was added and the cells plated; functionality and percentage of functional DNA were determined by measuring TNF levels with ELISA, as described in Example 1.

Transfection

DNA and lipid were mixed together in sterile polystyrene tubes; 1 ml serum-free plating medium was added and the mixture was incubated at 25° C. for 15 minutes. After aspiration of the medium, cells were washed twice with L-15, and 1 ml serum-free medium was added. The transfection mixture was then added, and the cells were placed at 37° C., 2% CO$_2$. Transfections were stopped after 6 hours by aspiration of the transfection mixture and addition of complete medium. The cells were then incubated as above until harvest. 60 mm culture dishes and a final volume of 2 ml per dish were used for all transfections. Cells maintained in culture longer than 24 hours underwent a daily medium change.

Example VI

Protocol for Phase I Clinical Trial Combining Adenovirus Type 5

Patients with incurable, recurrent, head and neck primaries that are not amenable to surgery will be eligible for this study.

A dose escalation of Adenovirus type 5 (Ad5) containing the Egr-TNF genetic construct will be injected into the tumor at $10^8$ to $10^{11}$ plaque forming units (PFU) per tumor using 2 injection sites and a 25 gauge 1.5 inch needle. Tumors will be injected each week on Mondays for 5 to 7 consecutive weeks.

Tumors will be irradiated on five succeeding days, generally Monday through Friday, at 2 Gy/day to a total dose of 50 to 70 Gy.

Evaluation of Response to Treatment

Patients will be evaluated on the basis of history/physical exam, vital signs, performance status, height/weight/BSA, CBC/Diff/Platelets, SMA-17, PT/PTT, CXR, EKG, serum TNF, and tumor measurements. Parameters will be measured during prestudy, at one week, and at the end of the study. Tumor measurements will be obtained when available by an appropriate study (x-rays, scans, tumor markers, etc.) during the prestudy period and within 2 to 4 weeks of completion of study.

Criteria for Response and Toxicity

Tumor Response—Both disease within and outside the radiation field will be evaluated independently; treatment will be evaluated according to the following criteria:
Complete Response (CR): Complete disappearance of all measurable and evaluable lesions for at least one month.
Partial Response (PR): Greater than 50% reduction in the products of the perpendicular diameters of marker lesions and no progression of any existing lesions or development of new lesions for at least one month.
Minor Response (MR): Greater than 25% and less than 50% reduction in the products of the perpendicular diameters of marker lesions and no progression of any existing lesions or development of new lesions for at least one month.
Stable Disease (S): Change in tumor size is less than that required for designation as a response or progression.
Progressive Disease (PD): Greater than 25% increase in the products of the perpendicular diameters of any existing lesions or the appearance of new lesions.
Relapse (R): Appearance of new lesions or reappearance of old lesions subsequent to a response.

Grading of Toxicity

Comprehensive assessments of toxicity will be performed throughout the study. Grading of toxicity will conform to the modified WHO Recommendations for Grading of Acute and Subacute Toxicity (Appendix C). A reduction in Karnofsky performance status (Appendix B) by 20% will be regarded as Grade 2 toxicity.

Management of Toxicity

Common side effects of parenteral rHuTNF include: fever, chills, myalgias, headache, nausea and vomiting, reversible thrombocytopenia, granulocytopenia, hypertriglyceridemia, hypercholesterolemia, moderate hypertension and elevations of transaminase and bilirubin. Less commonly, ischemic cardiac events and neurological deficits have been reported. A decline in the diffusion capacity of the lung have been reported. Acetaminophen and meperidine will be used to treat the constitutional symptoms. Lorazepam will be used preferentially for nausea and vomiting. Phenothiazines will be avoided.

Frequency of Toxicity Assessment

Prior to each weekly treatment, the principal investigator or co-investigator will fully assess the patient's condition with respect to possible treatment related toxicities. Such toxicity assessments are intended to be a comprehensive evaluation of the patient's condition during the period following the most recent exposure to the drug and/or since the previous toxicity assessment.

Grade 2 or greater toxicity that has not reversed by the time of further therapy will usually require interruption of rHuTNF until toxicity resolves.

Dose Modification and Determination of MTD

Patients who develop systemic grade 3 or 4 toxicity will not receive further gene therapy until the toxicity has improved; radiotherapy may be continued, however. Once the toxicity has improved to grade≦1, gene therapy may be resumed at adjusted doses:

For Grade 3 Toxicity, it will be necessary to decrease the doses of TNF by one level. If level 1 is being administered, 75% of the previous dose of TNF is administered. For Grade 4 Toxicity, the dose of TNF gene therapy is decreased by two levels. If level 1 or 2 is being administered, 50% of the previous dose of TNF is given.

Patients who develop grade 3 or 4 toxicity within the irradiated field will have all treatment held until the toxicity improves to grade≦1. Treatment may then be resumed according to the above guidelines.

If grade 3 or higher grades of toxicity occurs in one patient, a maximum of three more patients will be added at that dose level to further define the MTD. The MTD will be defined as the level at which 4 or more of 6 patients develop>grade 2 toxicity.

Example VII

Synergistic Killing of Cells Using Ionizing Radiation and Constitutive Promoters Operatively Linked to TNF-α

In Vitro TNF Production

Each cell line was grown to 80% confluence and inoculated with virus for 16 hours prior to irradiation. Lipofection was performed using DOTMA/DOPE and the Egr-TNF plasmid added to cell cultures for 6 hours. Transfected or infected cells were exposed to 20 Gy.

TNF ELISA was performed on samples from the medium at the indicated times.

Results:

High constitutive TNF production and release into the medium was observed for each cell line for 9 days following irradiation. No x-ray induction was observed following infection.

In vitro TNF Production

Radiation-Inducible TNF Expression (pg/mg Protein)
Liposome (10 μg Eqr-TNF Plasmid)

| | Liposome (10 μg Egr-TNF plasmid) | |
|---|---|---|
| | x-ray (20 Gy) + liposome | control (x-ray alone) |
| Pro4L | (24 hr) 81 ± 30 | 56 ± 7 |
| 1591 | 140 ± 36 | 83 ± 16 |

Example VIII

Tumor Cell Killing with HSV-1 (Egr-TNF), Ad5 (Egr-TNF), and X-Rays a. In Vitro Survival Analyses The HSV-1 mutant, 3636, has the γ34.5 region deleted, is replication deficient, and is cytotoxic to tumor cells. The Egr-TNF genetic construct was cloned into the R3616 mutant using Vero cells and standard cloning techniques (Sambrook et al., 1989). SQ-20B cells were grown to 90% confluence and inoculated with the Egr-TNF containing HSV-1 mutant R3616 (R899—6) at $10^3$ PFU/cell, a viral titer that minimally reduces plating efficiency. The cells were infected, and irradiated 5 hours later with 5 Gy. The cells were immediately subcultured at cell densities ranging from 500 to $1 \cdot 10^4$ cells/dish. After 10 to 12 days, colonies were stained and counted. The surviving fraction of cells was corrected for reduced plating efficiency with virus alone.

Results:

HSV-1 containing Egr-TNF reduced plating efficiencies (PE) of all 3 cell lines, while Ad5 containing Egr-TNF reduced PE for SQ-20B only. Synergistic killing was observed for all 3 cell lines with HSV-Egr-TNF, and for SQ-20B using Ad5-Egr-TNF.

| Adenovirus type 5 (MOI = 1) | | | |
|---|---|---|---|
| | 5 Gy | Ad5(TNF) alone | 5 Gy + Ad(TNF) |
| Pro4L | 0.33 | 0.83 | 0.31 |
| 1591 | 0.23 | 0.64 | 0.28 |
| SQ20B | 0.40 | 0.12 | 0.03 |

| HSV-1 (MOI = 0.001) | | | |
|---|---|---|---|
| | 5 Gy | HSV(TNF) alone | 5 Gy + HSV(TNF) |
| Pro4L | 0.33 | 0.38 | 0.1 |
| 1591 | 0.23 | 0.45 | 0.12 |
| SQ20B | 0.4 | 0.1 | 0.02 | b. In vivo Tumor Control using HSV-1 (Egr-TNF)

The SQ-20B squamous carcinoma cell line is radioresistant when compared to other human tumor cells in vivo ($D_0$=239) (Weichselbaum et al., 1985). The cells were grown in DMEM:F-12 (3:1), 20% fetal bovine serum, 0.4 µg/ml hydrocortisone, 100 units/ml penicillin, and 100 µg/ml streptomycin. The cells were trypsinized, washed in complete medium and injected subcutaneously into the right hind leg (thigh) of nude mice with 100 µl of cell suspension (106 to 5×10$^6$ cells) in PBS to form human tumor xenografts. The tumor diameters were measured twice weekly with calipers. The tumor volumes were calculated by the formula of a rotational ellipsoid $\pi/6 \times a \times b^2$ where a is the longer and b is the perpendicular shorter tumor axis (Baumann et al., 1992; Budach et al., 1993).

Once tumors reach 100 mm$^3$, the R899—6 HSV-1 mutant containing the Egr-TNF was injected at 10$^7$ PFU/tumor in 50 µl of milk based buffer. Animals were anesthetized with ketamine and verset during inoculation of tumors and irradiation. Six hours after inoculation, tumors were irradiated using a GE maxitron generator with 20 GY single dose using 150 kV at 2 Gy/min. Animals were shielded with lead excerpt for the limb containing the tumor. TNF ELISA was performed on tumors 3 days following irradiation, and tumors were measured as well.

Results:

TNF greater than 1000 pg/mg protein was produced in tumors treated with virus alone, while 300 pg/mg was detected in irradiated tumors. Tumors treated with both HSV-1 (Egr-TNF) and radiation regressed and did not regrow. The reduction in TNF following irradiation was presumed to be due to synergistic killing of infected cells.

| | HSV-1 (10$^3$ PFU/cell) | |
|---|---|---|
| | x-ray(20 Gy) | virus alone |
| SQ20B tumor: | 300 pg/mg controlled | >1000 pg/mg persistent | c. In Vivo TNF Expression (pg/mg Protein) and Tumor Control with AD5 (Egr-TNF)

SQ-20B xenografts or Pro4L tumors were inoculated with 10$^9$ PFU and irradiated. TNF ELISA was performed on tumors 24 hr following irradiation. Controls are virus alone.

Results:

In Pro4L tumors, TNF 6667 pg/mg protein was produced in tumors treated with virus alone, while 3700 pg/mg was produced following irradiation. This reduction is likely due to killing of infected cells.

| Adenovirus type 5 (1 PFU/cell) | | |
|---|---|---|
| | 5 Gy | 20 Gy | virus alone |
| 1591 | | 3700 | 6667 |
| SQ20B | | 9643 (day 4) | 10480 (day 10) |

Example IX

Human Gene Transfer Protocols

This prophetic example describes some of the ways in which the present invention is envisioned to be of use in the treatment of human disorders via gene therapy, such as, for example, in the treatment of neoplasia or hyperplasia in a subject.

Human subjects for whom the medical indication for adenovirus-mediated TNF gene transfer or increased expression of TNF has been established would be tested for the presence of antibodies directed against adenovirus. If antibodies are present and the patient has a history of allergy to either pharmacological or naturally occurring substances, application of a test dose of on the order of 10$^8$ to 10$^{12}$ recombinant adenovirus in a dose escalation study under close clinical observation would be indicated.

Recombinant adenovirus expressing TNF or other toxin is prepared and purified by any method that would be acceptable to the Food and Drug Administration for administration to human subjects, including, but not limited to cesium chloride density gradient centrifugation, and subsequently tested for efficacy and purity. Virus is administered to patients by means of direct tumor inoculation or intravenous administration in any pharmacologically acceptable solution, either as a bolus or as an infusion over a period of time. Generally speaking, it is believed that the effective number of functional virus particles to be administered would range from 10$^9$ to 10$^{10}$ in a dose escalation study.

Patients would remain hospitalized during the trial for at least 48 hrs. to monitor acute and delayed adverse reactions.

Further possible follow-up examinations include obtaining of biopsy material in which the pattern of expression of the transferred gene could be directly assessed. This would also supply information about the number of cells that have taken up the transferred gene and about the relative promoter strength in the particular tissue. Based on the data obtained, adjustments to the treatment may be desirable. These adjustments might include adenovirus constructs that use different promoters or a change in the number of pfu injected to ensure a homogeneous infection of all tumor cells without unphysiological overexpression of the recombinant gene. Although the latter is not considered as a potential danger to the patient, the aim of the gene transfer should generally be to adjust TNF levels to sub toxic levels.

Example X

Use of Tumor Infiltrating Lymphocytes to Deliver Constructs to Cells Prior to Irradiation Growth of TIL Procedures for the growth of human TIL have been already published. In brief, freshly resected tumor is minced into 3- to 5-mm$^3$ fragments and digested over-night in an enzyme medium consisting of collagenase type IV, hyaluronidase type V, and deoxyribonuclease type IV. The next day, the single-cell suspension is passed through a sterile wire mesh grid to remove undigested debris, the cells were washed three times, and viable cells are counted. If viability is less than 70% or the preparation was heavily contaminated with erythrocytes, the preparation is separated by Ficoll-Hypaque (Organon Teknica-Cappel, Durham, N.C.) gradient centrifugation to remove dead cells and erythrocytes and then washed again in saline solution.

The cell cultures are established by plating 5×10$^5$/mL of total cells of the single-cell suspension in culture medium composed of either serum-free AIM-5 medium (GIBCO, Grand Island, N.Y.) or RPMI-1640 medium containing 10% human AB serum, with the additives, glutamine, amphotericin B, penicillin, streptomycin, 7200 IU/mL of IL-2, and 10% LAK cell supernatant. During the course of 2 weeks, the tumor cells will gradually disappear as the lymphocytes grow. When the lymphocyte number reaches 1.5×10$^6$ cells/mL, these cells were split with fresh medium. When approximately 10$^9$ cells are reached, the cells are switched from tissue culture plates to gas-permeable cell culture bags and cultured until greater than 10$^{11}$ TIL are obtained.

To administer TIL, they are first collected in saline using continuous-flow centrifugation and then filtered through a platelet administration set into a volume of 200 to 300 mL containing albumin and 450,000 IU of IL-2. The TIL are infused into patients over 30 to 60 minutes through a central venous catheter.

Clinical Protocol

The patients will receive up to 3×10$^{11}$ TIL containing Egr-TNF administered in one to four infusions of up to 300 mL each. Approximately 2 hours after completing the TIL infusions, the patients will receive intravenous administration of recombinant TNF every 8 hours varying doses depending on the protocol.

Those receiving TIL modified by the TNF gene will receive escalating doses of transduced TIL alone, starting at 108 TIL and escalating every 3 to 7 days to a final level of 3×10$^{11}$ TIL.

Example XI

Method of Assessing the In Vitro Efficacy of Radiosensitizing or Radioprotecting Factors in Cells Cells in culture that are to be tested are transfected with a genetic construct as set forth in the above examples. Radiation is given as described in example 1. In brief, each cell line will be grown to 80% confluence and transfected with the genetic construct for approximately 16 hours prior to irradiation. Transfection will be accomplished by any of the above-described methods, however for the purposes of this example, lipofection will be performed using DOTMA/DOPE and the genetic construct containing the gene encoding the protein of interest will be added to cell cultures for 6 hours. Transfected or infected cells are then exposed to 20 Gy ionizing radiation. To assess the function of the protein of interest in concert with the ionizing radiation, ELISA will be performed on the medium samples, and cell survival studies will be performed as indicated in example VIII.

The invention also concerns methods of in vitro testing to assess the responses of different cells to selected radiosensitizing or radioprotecting factors, determining if the cells respond to that particular factor and the radiation dose in a synergistic or additive manner. A particular advantage of this method is that it allows the skilled artisan and clinician to make choices relating to the selection of radiosensitizing or radioprotective agents to use in treatment protocols, based on the cell type to be treated.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ainsworth, E. J. and H. B. Chase, (1959) Effect of microbial antigens on irradiation mortality in ice, *Proc. Soc. Exp. Biol. Med.*, 102: p. 483.

Baumann, M., DuBois, W., Pu, A., Freeman, J., Suit, H. (1992) Response of Xenografts of Human Malignant Gliomas and Squamous Cell Carcinomas to Fractionated Irradiation. *Int. J. Radiat. Oncol. Biol. Phys.* 23, pp. 803-809.

Beutler, B., Cerami, A. (1988) Tumor Necrosis, Cachexia, Shock, and Inflammation: A Common Mediator. *Annu. Rev. Biochem.* 57, pp. 505-518.

Brach, M. A., Hass, R., Sherman, M. L., Gunji, H., Weichselbaum, R., Kufe, D. (1991) Ionizing radiation Induces Expression and Binding Activity of the Nuclear Factor kB. *J. Clin. Invest.* 88, pp. 691-695.

Budach, W., Budach, V., Stuschke, M., Dinges, S., Sack, H. (1993) The TCD$_{50}$ and Regrowth Delay Assay in Human Tumor Xenografts: Differences and Implications. *Int. J. Radiat. Oncol. Biol. Phys.* 25, pp. 259-268.

Carswell, E. A., Old, L. J., Russel, R. L., Green, M., Williamson, B. (1975) Tumor Necrosis Factor α. *Proc. Natl. Acad. Sci.* 72, pp. 3600-3670.

Chou, J. and Roizman, B., (1992) *Proc. Natl. Acad. Sci.* 89, pp. 3266-3270.

Couch, R. B., R. M. Chanock, T. R. Cate, D. J. Lang, V. Knight, and R. J. Huebner. 1963. Immunization with types 4 and 7 adenovirus by selective infection of the intestinal tract. *Am. Rev. Resp. Dis.* 88: 394-403.

Datta, R., Hallahan, D., Kharbanda, S., Rubin, E., Sherman, M., Huberman, E., Weichselbaum, R. R., Kufe, D. (1992) Involvement of Reactive Oxygen Intermediates in the Activation of c-jun Gene Transcription by Ionizing radiation. *Biochemistry* 31, pp. 8300-8306.

Datta, R., Tanej, A., Sukhatme, V., Qureski, S. A., Weichselbaum, R. R., Kufe, D. W. (1993) Reactive Oxygen Intermediates Target CArG Sequences to Mediate Activation of the Immediate Early Transcription Factor Egr-1 by Ionizing Radiation. *Proc. Natl. Can. Sci.* 90, pp. 2419-2423.

Datta, R., Rubin, E., Sukhatme, V., Quershi, S., Hallahan, D. E., Weichselbaum, R. R., Kufe, D. (1992) Ionizing Radiation Activates Transcription of the Egr-1 Gene via CArG Elements. *Proc. Natl. Sci.* 89, pp. 10149-10153.

Felgner, P. L. et al. (1987) Proc. Natl. Acad. Sci. USA 84, 7413-7417.

Felgner, P. et al. (1987) *Proc. Natl. Acad. Sci. U.S.A.* 84, 7413.

Gashler, A. L., Swaminathan, S., Sukhatme, V. P. (1993) A Novel Repression Module, an Extensive Activation Domain, and a Bipartite Nuclear Localization Signal Defined in Immediate-Early Transcription Factor Egr-1. *Molecular and Cellular Biology* 13, pp. 4556-4571.

Ghosh-Choudhury, G., Y. Haj-Ahmad, and F. L. Graham. 1987. Protein IX, a minor component of the human adenovirus capsid, is essential for the packaging of full-length genomes. *EMBO J.* 6: 1733-1739.

Gomez-Foix, A. M., W. S. Coats, S. Baque, T. Alam, R. D. Gerard, and C. B. Newgard. 1992. Adenovirus-mediated transfer of the muscle glycogen phosphorylase gene into hepatocytes confers altered regulation of glycogen. *J. Biol. Chem.* 267: 25129-25134.

Graham, F. L., and L. Prevec. 1992. Adenovirus-based expression vectors and recombinant vaccines. *Biotechnology* 20: 363-390.

Graham, F. L., J. Smiley, W. C. Russell, and R. Nairn. 1977. Characteristics of a human cell line transformed by DNA from human adenovirus type 5. *J. Gen. Virol.* 36: 59-72.

Graham, F. L. 1984. Covalently closed circles of human adenovirus DNA are infectious. *EMBO J.* 3: 3917-2922.

Graham, F. L., and L. Prevec. 1991. Manipulation of adenovirus vectors. In: Methods in Molecular Biology (Vol. 7), Gene Transfer and Expression Protocols, ed. E. J. Murray, The Humana Press Inc., Clifton, N.J.

Grunhaus, A., and M. S. Horwitz. 1992. Adenoviruses as cloning vectors. *Semin. Virol.* 3: 237-252.

Hallahan, et al., (1989) Increased tumor necrosis factor alpha mRNA after cellular exposure to ionizing radiation. *Proc. Natl. Acad. Sci. USA*, 86(24): p. 10104-7.

Hallahan, D. E., Beckett, M. A., Kufe, D. Weichselbaum, R. R. (1990) The Interaction between Human Recombinant Tumor Necrosis Factor and Radiation in 13 Human Tumor Cell Lines. *Int. J. Radiat. Oncol. Biol. Phys.* 19, pp. 69-74.

Hallahan, D. E., Weichselbaum, R. R., Rubin, S., Vijayakumar, S., Samuels, B., Phillips, R., Kufe, D., O'Brien, S., Vokes, E. (1993) Phase I Dose Escalation Study of Tumor Necrosis Factor and Radiation. *Int. J. Radiat. Oncol. Biol. Phys.* 27(1) Abstract #94, p. 184.

Hallahan, D. E., Guis, D., Kuchibhotia, J., Sukhatme, V., Kufe, D. W., Weichselbaum, R. R. (1992) Radiation Signalling Mediated by Jun Activation Following Dissociation from a Cell-Type Specific Repression. *J. Biol. Chem.* 268, pp. 4903-4907.

Herz, J., and R. D. Gerard. 1993. Adenovirus-mediated transfer of low density lipoprotein receptor gene acutely accelerates cholesterol clearance in normal mice. *Proc. Natl. Acad. Sci. USA* 90: 2812-2816.

Jones, N., and T. Shenk. 1978. Isolation of deletion and substitution mutants of adenovirus type 5. *Cell* 13: 181-188.

Larrick, J. W. a. S. C. W., (1990) Cytotoxic mechanism of tumor necrosis factor-a. FASEB J., 4: p. 3215-3223.

Le Gal La Salle, G., J. J. Robert, S. Berrard, V. Ridoux, L. D. Stratford-Perricaudet, M. Perricaudet, and J. Mallet. 1993. An adenovirus vector for gene transfer into neurons and glia in the brain. *Science* 259: 988-990.

Levrero, M., V. Barban, S. Manteca, A. Ballay, C. Balsamo, M. L. Avantaggiati, G. Natoli, H. Skellekens, P. Tiollais, and M. Perricaudet. 1991. Defective and nondefective adenovirus vectors for expressing foreign genes in vitro and in vivo. *Gene* 101: 195-202.

Matthews, N., et al., (1987) Tumor cell killing by TNF inhibited by anaerobic conditions, free radical scavengers and inhibitors of arachadonate metabolism. *Immunology*, 62: p 153-155.

Mukherjee, A. B. et al. (1978) *Proc. Natl. Acad. Sci. USA* 75, 1361-1365.

Neta, R. Oppenheim, J. J. (1991) Radioprotection with Cytokines—Learning from Nature to Cope with Radiation Damage. *Cancer Cells* 3, pp. 391-396.

Neta, R. and J. Oppenheim, (1988) 149: p. 108-111.

Neta, R. et al., (1991) Role of cytokines (interleukin 1, tumor necrosis factors, and transforming growth factor beta) in natural and lipopolysaccharide-enhanced radioresistance. *J. Exp. Med.*, 173: p. 1177-1182.

Nicolau, C. et al. (1983) *Proc. Natl. Acad. Sci. USA* 80, 1068-1072.

Old, L. J. (1988) in *Tumor Necrosis Factor/Cachectin and Related Cytokines*, eds. Bonavida, B., Gifford, G. E., Kirchner, H., Old, L. J. (Basel, Switzerland, S. Karger) pp. 7-19.

Old, L. J. (1988) Tumor Necrosis Factor α. *Sci. Amer.* 258, pp. 59-75.

Post and Roizman *Cell*, 25: 227, 1981.

Ragot, T., N. Vincent, P. Chafey, E. Vigne, H. Gilgenkrantz, D. Couton, J. Cartaud, P. Briand, J.-C. Kaplan, M. Perricaudet, and A. Kahn. 1993. Efficient adenovirus-mediated transfer of a human minidystrophin gene to skeletal muscle of mdx mice. *Nature* 361: 647-650.

Reid, T. et al., (1991) Resistance to killing by tumor necrosis factor in an adipocyte cell line caused by a defect in arachidonic acid biosynthesis. *J. Biol. Chem.*, 266(25): p. 16580-16586.

Rich, D. P., L. A. Couture, L. M. Cardoza, V. M. Guiggio, D. Armentano, P. C. Espino, K. Hehir, M. J. Welsh, A. E. Smith, and R. J. Gregory. 1993. Development and analysis of recombinant adenoviruses for gene therapy of cystic fibrosis. *Hum. Gene Ther.* 4: 461-476.

Roizman, R., and A. E. Sears. 1990. Herpes simplex viruses and their replication, In: Virology, (2nd ed), eds. B. N. Field, D. M. Knipe, R. M. Chanock, J. L. Melnick, M. S. Hirsch, T. P. Monath, B. Roizman. pp. 1795-1841. Raven Press, New York.

Rosenfeld, M. A., W. Siegfried, K. Yoshimura, K. Yoneyama, M. Fukayama, L. E. Stier, P. K. Paakko, P. Gilardi, L. Stratford-Perricaudet, M. Perricaudet, S. Jallat, A. Pavirani, J.-P. Lecocq, and R. G. Crystal. 1991. Adenovirus-mediated transfer of a recombinant α1-antitrypsin gene to the lung epithelium in vivo. *Science* 252: 431-434.

Rosenfeld, M. A., K. Yoshimura, B. C. Trapnell, K. Yoneyama, E. R.

Rosenthal, W. Dalemans, M. Fukayama, J. Bargon, L. E. Stier, L. Stratford-Perricaudet, M. Perricaudet, W. B. Guggino, A. Pavirani, J.-P. Lecocq, and R. G. Crystal. 1992. In vivo transfer of the human cystic fibrosis transmembrane conductance regulator gene to the airway epithelium. *Cell* 68: 143-155.

Sambrook et al. (1989). Molecular cloning: A laboratory manual. Cold Spring Harbor Laboratory. Cold Spring Harbor, N.Y.

Sersa, G., Willingham, V., Milas, L. (1988) Anti-tumor Effects of Tumor Necrosis Factor Alone or Combined with Radiotherapy. *Int. J. Cancer* 42, pp. 129-134.

Stratford-Perricaudet, L., and M. Perricaudet. 1991. Gene transfer into animals: the promise of adenovirus. p. 51-61, In: *Human Gene Transfer*, Eds, O. Cohen-Haguenauer and M. Boiron, Editions John Libbey Eurotext, France.

Tartaglia, L. A., Goeddel, D. V. (1992) Two TNF Receptors. *Immunology Today* 13, pp. 151-153.

Tartaglia, L. A., Rotha, M., Hu, Y. F., Goeddel, D. V. (1993) Tumor Necrosis Factor's Cytotoxic Activity is Signaled by the p55 TNF Receptor. *Cell* 73, pp. 213-216.

Tartaglia, L. A., Ayers, M., Wong, G. H. W., Goeddel, D. V. (1993) A Novel Domain Within the 55 kd TNF Receptor Signals Cell Death. *Cell* 74, pp. 845-853.

Tartaglia, L. A., Goeddel, D. V. (1992) Tumor Necrosis Factor Receptor Signaling. *J. Biol. Chem.* 267, pp. 4304-4307.

Teng, M. N., Park, B. H., Koeppen, K. W., Tracey, K. J., Fendly, B. M., Schreiber, H. (1991) Long-term Inhibition of Tumor Growth by Tumor Necrosis Factor in the Absence of Cachexia or T-cell Immunity. *Proc. Natl. Acad. Sci.* 88, pp. 3535-3539.

Thomsen, D. R., Stenberg, R. M., Goins, W. F., and Stinski, M. F. (1984) *Proc. Natl. Acad. Sci. USA,* 81, 659-663

Top, F. H., Jr., El. L. Buescher, W. H. Bancroft, and P. K. Russell. 1971. Immunization with live types 7 and 4 adenovirus vaccines. II. Antibody response and protective effect against acute respiratory disease due to adenovirus type 7. *J. Infect. Dis.* 124: 155-160.

Vogel, S. N. and M. Hogan, (1990) Role of cytokines in endotoxin-mediated host responses. *Immunophysiology*, Role of Cells and Cytokines in Immunity and Inflammation, ed. a.E.N.S.J.J. Oppenheim. London: Oxford University Press. 238-258.

Weichselbaum, R. R. (1991) Possible Applications of Biotechnology to Radiotherapy. *Eur. J. Can.* 47, pp. 405-407.

Weichselbaum, R. R., Hallahan, D. E., Sukhatme, V., Dritschilo, A., Sherman, J. L., Kufe, D. W. (1991) Biological Consequences of Gene Regulation Following Ionizing Radiation. *J. Natl. Cancer Inst.* 83, pp. 480-484.

Weichselbaum, R. R., Hallahan, D. H., Sukhatme, V. P., Kufe, D. W. (1992) Gene Therapy Targeting by Ionizing Radiation. *Int. J. Radiat. Oncol. Biol. Phys.* 24, pp. 565-567.

Weichselbaum, R. R., Dahlberg, W., Little, J. B. (1985) Inherently Radioresistant Cells Exist in Some Human Tumors. *Proc. Natl. Acad. Sci.* 82, pp. 4732-4735.

Wong, G. H., Tartaglia, L. A., Lee, M. S., Goeddell, D. V. (1992) Antiviral Activity of Tumor Necrosis Factor is Signaled Through the 55-kDa Type 1 TNF Receptor. *J. Immunol.* 149, pp. 3550-3553.

Wong, G. H. W. and D. V. Goeddel, (1988) Induction of manganous superoxide dismutase by tumor necrosis factor: Possible protective mechanism. *Science,* 242: p. 941-944.

Wong, G. H., McHugh, T., Weber, R., Goeddel, D. V. (1991) Tumor Necrosis Factor Selectively Sensitizes Human Immunodeficiency Virus-Infected Cells to Heat and Radiation. *Proc. Natl. Acad. Sci. USA* 88, pp. 4372-4376.

Yamauchi, N., Karizana, H., Wantanbe, H., Neda, H., Maeda, M., Nutsu, Y. (1989) Intracellular Hydroxyl Radical Production Induced by Recombinant Human Tumor Necrosis Factor. *Cancer Res.* 49, pp. 1671-1675.

Zimmerman, R. J., Chan, A., Leadon, F. A. (1989) Oxidative Damage in Murine Tumor Cells Treated In Vitro by Recombinant Human Necrosis Factor. *Cancer Res.* 49, pp. 1644-1648.

What is claimed is:

1. A process of treating a human cancer patient comprising providing to a cancer cell in said patient a nucleic acid encoding a radiosensitizing polypeptide operatively linked to a constitutive promoter and contacting said cell with ionizing radiation, whereby the nucleic acid is expressed to produce the radiosensitizing polypeptide and the cancer is treated.

2. The process of claim 1, wherein the nucleic acid encodes a TNF-α.

3. The process of claim 1, wherein the constitutive promoter is the immediate-early CMV enhancer/promoter, the RSV enhancer/promoter, the SV40 early promoter, the SV40 late enhancer/promoter, the MMSV LTR, the SFFV enhancer/promoter, the EBV origin of replication, the β-actin promoter or the Egr enhancer/promoter.

4. The process of claim 1, wherein said nucleic acid is provided by transfection by liposomes, adenovirus or HSV-1.

5. The process of claim 4, wherein the liposome comprises DOTMA, DOTMA/DOPE, or DORIE.

6. The process of claim 4, wherein the transfection is by adenovirus infection.

7. The process of claim 4, wherein the transfection is by HSV-1 infection.

8. A process of sensitizing a cell to the effects of ionizing radiation comprising transfecting the cell with an adenovirus vector construct comprising a nucleic acid that encodes a cytokine, wherein said cytokine is synthesized in and secreted from said cell.

9. The process of claim 8, wherein the nucleic acid that encodes the cytokine is positioned under control of a promoter other than an adenovirus promoter.

10. The process of claim 9, wherein the promoter is the immediate-early CMV enhancer/promoter, the RSV enhancer/promoter, the SV40 early promoter, the SV40 late enhancer/promoter, the MMSV LTR, the SFFV enhancer/promoter, the EBV origin of replication, the β-actin promoter or the Egr enhancer/promoter.

11. A process of radioprotecting a cell from the effects of ionizing radiation comprising:
   (a) obtaining a genetic construct comprising a nucleic acid encoding a cell radioprotecting factor operatively linked to a constitutive promoter; and
   (b) transfecting a cell with the genetic construct;
whereby said radioprotecting factor is expressed and said cell is protected from said effects.

12. The process of claim 11, wherein the radioprotecting factor is MnSOD, IL-1 or IL-2.

13. The process of claim 11, wherein the transfecting is by liposomes, adenovirus, or HSV-1.

14. The process of claim 13, wherein the liposome comprises DOTMA, DOTMA/DOPE, or DORIE.

15. The process of claim 13, wherein the transfection is by adenovirus infection.

16. The process of claim 13, wherein the transfection is by HSV-1 infection.

17. A process of radioprotecting a cell from the effects of ionizing radiation comprising transfecting the cell with an adenovirus vector construct comprising a nucleic acid encoding a radioprotecting factor in a mammalian cell.

18. The process of claim 17, wherein the nucleic acid is positioned under control of a promoter other than an adenovirus promoter.

19. The process of claim 18, wherein the promoter is the immediate-early CMV enhancer/promoter, the RSV enhancer/promoter, the SV40 early promoter, the SV40 late enhancer/promoter, the MMSV LTR, the SFFVs enhancer/promoter, the EBV origin of replication, the β-actin promoter or the Egr enhancer/promoter.

20. A method of expressing a radioprotecting or radiosensitizing factor in a mammal comprising administering to the mammal an effective amount of a pharmaceutical composition comprising a genetic construct comprising a nucleic acid that encodes a TNF-α operatively linked to a constitutive promoter dispersed in a pharmacologically acceptable carrier, wherein the genetic construct is packaged within an adenovirus particle.

21. The method of claim 20, wherein the administering is by means of an intravenous injection of from $10^8$ to $10^{11}$ virus particles.

22. The method of claim 20, wherein the mammal is a mouse.

23. The method of claim 20, wherein the mammal is a human.

24. A process of inhibiting growth of a tumor comprising the steps of:
    (a) delivering to said tumor a therapeutically effective amount of a DNA molecule comprising a constitutive promoter operatively linked to a region encoding a polypeptide having the ability to inhibit growth of a tumor cell, which coding region further is operatively linked to a transcription—terminating region, whereby said polypeptide is expressed; and
    (b) exposing said cell to an effective dose of ionizing radiation, whereby the growth of said tumor is inhibited by said polypeptide and ionizing radiation.

25. A method of assessing the response of a cell to the constitutive production of radiosensitizing or radioprotecting factors following ionizing radiation comprising:
    (a) growing the cell in culture;
    (b) transfecting the cell with a genetic construct comprising a nucleic acid that encodes the cell radiosensitizing factor or radioprotecting factor operatively linked to a constitutive promoter, whereby said nucleic acid is expressed to produce the radiosensitizing factor or radioprotecting factor;
    (c) exposing the cell to an effective dose of ionizing radiation; and
    (d) assessing the response of the cell.

26. A process of inhibiting growth of a tumor in a host comprising the steps of:
    (a) injecting into the tumor a therapeutically effective amount of a pharmaceutical composition comprising a genetic construct comprising a nucleic acid that encodes a TNF-α operatively linked to a constitutive promoter dispersed in a pharmacologically acceptable carrier, wherein the genetic construct is packaged within an adenovirus particle, and
    (b) administering to the host an effective dose of ionizing radiation,
    whereby the growth of the tumor is inhibited by expression of the nucleic acid encoding a TNF-α and the administration of ionizing radiation.

27. The process of claim 26, wherein the amount of the pharmaceutical composition is between $10^8$ and $10^{11}$ plaque forming units.

28. The process of claim 26, wherein the total dose of ionizing radiation is between 50 and 70 Gray.

29. The process of claim 24, wherein the polypeptide is a TNF-α.

30. The process of claim 8, wherein the cytokine is a TNF-α.

* * * * *